US012193625B2

(12) United States Patent
Boyer et al.

(10) Patent No.: US 12,193,625 B2
(45) Date of Patent: Jan. 14, 2025

(54) HIGH SPEED REUSABLE BEVERAGE CONTAINER WASHING SYSTEM WITH POP-UP ULTRAVIOLET SANITIZER

(71) Applicant: Midea Group Co., Ltd., Foshan (CN)

(72) Inventors: Joel Boyer, Louisville, KY (US); Robert M. Digman, Goshen, KY (US)

(73) Assignee: MIDEA GROUP CO., LTD., Guangdong (CN)

( * ) Notice: Subject to any disclaimer, the term of this patent is extended or adjusted under 35 U.S.C. 154(b) by 414 days.

(21) Appl. No.: 17/674,930

(22) Filed: Feb. 18, 2022

(65) Prior Publication Data
US 2023/0263363 A1    Aug. 24, 2023

(51) Int. Cl.
| A47L 15/42 | (2006.01) |
| A47L 15/00 | (2006.01) |
| A61L 2/10 | (2006.01) |
| A61L 2/22 | (2006.01) |
| B05B 3/12 | (2006.01) |

(52) U.S. Cl.
CPC ......... *A47L 15/428* (2013.01); *A47L 15/0065* (2013.01); *A47L 15/0076* (2013.01); *A47L 15/4242* (2013.01); *A61L 2/10* (2013.01); *A61L 2/22* (2013.01); *B05B 3/12* (2013.01); *A61L 2202/122* (2013.01); *A61L 2202/15* (2013.01); *A61L 2202/17* (2013.01); *A61L 2202/23* (2013.01)

(58) Field of Classification Search
None
See application file for complete search history.

(56) References Cited

U.S. PATENT DOCUMENTS

| 1,502,131 A | 2/1922 | Vaudreuil |
| 1,876,895 A | 9/1932 | James |
| 2,263,807 A | 11/1941 | Hanson |
| 2,634,736 A | 4/1953 | Bewen |
| 2,764,171 A | 9/1956 | Nolte |
| 2,970,700 A | 2/1961 | Lacy et al. |
| 3,060,946 A | 10/1962 | David |

(Continued)

FOREIGN PATENT DOCUMENTS

| CN | 2834716 Y | 11/2006 |
| CN | 201529653 U | 7/2010 |

(Continued)

OTHER PUBLICATIONS

WO 2011129539 A2 translation, Device for Washing Cups, Kim (Year: 2011).*

(Continued)

*Primary Examiner* — Cristi J Tate-Sims
(74) *Attorney, Agent, or Firm* — Gray Ice Higdon

(57) ABSTRACT

A beverage container washing system may be used for rapid washing and/or sanitizing of beverage containers, e.g., for use in a retail environment to wash and/or sanitize customer-provided beverage containers prior to filling the beverage containers with purchased beverages, among other applications. The beverage container washing system may include a pop-up ultraviolet sanitizer that may be used to sanitize an interior of a beverage container by extending into an opening of the beverage container and emitting ultraviolet light onto an interior surface of the beverage container.

18 Claims, 14 Drawing Sheets

(56) References Cited

U.S. PATENT DOCUMENTS

| | | | |
|---|---|---|---|
| 3,204,273 | A | 9/1965 | Gallo |
| 3,312,230 | A | 4/1967 | Thring |
| 3,620,232 | A | 11/1971 | Angelo |
| 3,969,137 | A | 7/1976 | Jenkins |
| 4,444,213 | A | 4/1984 | Taylor |
| 4,561,904 | A | 12/1985 | Eberhardt, Jr. |
| 4,634,052 | A | 1/1987 | Grizzle et al. |
| 4,681,260 | A | 7/1987 | Cochran |
| 5,315,729 | A | 5/1994 | Yang |
| 5,343,886 | A | 9/1994 | Beswick |
| 5,522,410 | A | 6/1996 | Meilleur |
| 5,531,383 | A | 7/1996 | Pacht et al. |
| 5,640,981 | A | 6/1997 | Niemela et al. |
| 5,704,380 | A | 1/1998 | Zelniker et al. |
| 5,903,944 | A | 5/1999 | Burrell |
| 5,904,163 | A | 5/1999 | Inoue et al. |
| 6,110,424 | A | 8/2000 | Maiden et al. |
| 6,517,776 | B1 | 2/2003 | Rodgers et al. |
| 6,579,495 | B1 | 6/2003 | Maiden |
| 6,691,536 | B2 | 2/2004 | Severns et al. |
| 6,732,950 | B2 | 5/2004 | Ingham, Jr. et al. |
| 6,799,732 | B2 | 10/2004 | Sirkin |
| 6,926,017 | B2 | 8/2005 | Halbmaier |
| 7,882,591 | B2 | 2/2011 | Arnold |
| 8,136,742 | B2 | 3/2012 | Cordua |
| 8,297,533 | B2 | 10/2012 | Dunn et al. |
| 8,303,728 | B2 | 11/2012 | Peukert et al. |
| 8,500,919 | B1 | 8/2013 | Al-qaffas |
| 8,905,014 | B2 | 12/2014 | Shaffer |
| 9,138,768 | B2 | 9/2015 | Jahan et al. |
| 9,378,988 | B2 | 6/2016 | Osada et al. |
| 9,566,617 | B2 | 2/2017 | Jensen et al. |
| 9,596,972 | B2 | 3/2017 | Sonoda |
| 9,623,447 | B2 | 4/2017 | Kataoka |
| 9,707,306 | B2 | 7/2017 | Farren |
| 10,415,176 | B2 | 9/2019 | Abramovich et al. |
| 10,893,790 | B2 | 1/2021 | Ashworth et al. |
| 2003/0150475 | A1 | 8/2003 | Abrams et al. |
| 2004/0250837 | A1 | 12/2004 | Watson |
| 2005/0230638 | A1 | 10/2005 | Ancona et al. |
| 2006/0011263 | A1 | 1/2006 | Till |
| 2007/0246071 | A1 | 10/2007 | Streb |
| 2010/0071724 | A1* | 3/2010 | Baumgartner ............ B08B 9/34 134/166 R |
| 2011/0203616 | A1 | 8/2011 | Berner et al. |
| 2012/0141322 | A1 | 6/2012 | Fogg |
| 2014/0332041 | A1 | 11/2014 | Feddema |
| 2015/0182103 | A1 | 7/2015 | Jung |
| 2018/0028044 | A1 | 2/2018 | Anim-Mensah et al. |
| 2018/0092505 | A1 | 4/2018 | Simon |
| 2018/0168428 | A1 | 6/2018 | Wilson |
| 2018/0236398 | A1 | 8/2018 | Heer et al. |
| 2018/0318886 | A1 | 11/2018 | Libbrecht et al. |
| 2018/0338665 | A1 | 11/2018 | Foehringer |
| 2018/0354467 | A1 | 12/2018 | Glickman et al. |
| 2020/0216332 | A1 | 7/2020 | Li |
| 2020/0230267 | A1 | 7/2020 | Greenfield |
| 2020/0237179 | A1 | 7/2020 | Haegermarck |
| 2020/0253450 | A1 | 8/2020 | Kafzan et al. |
| 2020/0289685 | A1 | 9/2020 | Li |
| 2021/0161356 | A1 | 6/2021 | Luu et al. |
| 2022/0079413 | A1 | 3/2022 | Longo et al. |
| 2023/0095081 | A1 | 3/2023 | Boyer et al. |
| 2023/0097782 | A1 | 3/2023 | Trice et al. |
| 2023/0100978 | A1 | 3/2023 | Boyer et al. |
| 2023/0101333 | A1 | 3/2023 | Boyer et al. |
| 2023/0101384 | A1 | 3/2023 | Longo et al. |
| 2023/0101450 | A1 | 3/2023 | Boyer et al. |
| 2023/0102987 | A1 | 3/2023 | Boyer et al. |
| 2023/0112411 | A1 | 4/2023 | Digman et al. |

FOREIGN PATENT DOCUMENTS

| | | | | |
|---|---|---|---|---|
| CN | 101940459 | A | 1/2011 | |
| CN | 102324396 | A | 1/2012 | |
| CN | 203426095 | U | 2/2014 | |
| CN | 204363929 | U | 6/2015 | |
| CN | 205110293 | U | 3/2016 | |
| CN | 105534437 | A | 5/2016 | |
| CN | 109876169 | A | 6/2019 | |
| CN | 209915722 | U | 1/2020 | |
| CN | 209967112 | U | 1/2020 | |
| CN | 212166190 | U | 12/2020 | |
| CN | 213191400 | U | 5/2021 | |
| CN | 213551016 | U | 6/2021 | |
| DE | 4229250 | A1 | 3/1994 | |
| DE | 19618770 | A1 | 11/1997 | |
| DE | 102012109360 | A1 | 5/2014 | |
| EP | 1120121 | A2 * | 8/2001 | ............ A61L 2/10 |
| EP | 1183983 | A2 | 3/2002 | |
| EP | 3967207 | A1 | 3/2022 | |
| ES | 1265944 | U | 4/2021 | |
| FR | 1426408 | A | 1/1966 | |
| FR | 3068232 | A1 | 1/2019 | |
| GB | 309878 | A | 4/1929 | |
| IL | 108864 | A | 3/1999 | |
| JP | 2001247108 | A | 9/2001 | |
| KR | 101630417 | B1 | 6/2016 | |
| KR | 20160065051 | A | 6/2016 | |
| KR | 20180051462 | A | 5/2018 | |
| KR | 101885722 | B1 | 9/2018 | |
| KR | 101983721 | B1 | 5/2019 | |
| KR | 101987953 | B1 | 6/2019 | |
| KR | 102052837 | B1 | 12/2019 | |
| WO | WO0244637 | A1 | 6/2002 | |
| WO | WO2005087276 | A2 | 9/2005 | |
| WO | WO2007038904 | A1 | 4/2007 | |
| WO | WO2010132022 | A2 | 11/2010 | |
| WO | WO2020083851 | A1 | 4/2020 | |
| WO | WO2020212927 | | 10/2020 | |
| WO | 2021116749 | A1 | 6/2021 | |

OTHER PUBLICATIONS

Related Applications Transmittal.

YBB, YBB Professional Cup Washing Machine Tables Glass Rinser, Pitcher Rinser for Bar Café Household (Counter Top), retrieved from: https://www.amazon.com/YBB-Professional-Pitcher-Plating-Household/dp/B01MG7GPIR; Oct. 31, 2016.

Jectse, Cup Rinser, Automatic Household Commercial Cup Washer High-Pressure Cup Washer Cleaner Rinser Bar Accessories Home, Restaurant, Bar, Tea Shop, Coffee Shop, etc., Retrieved from: https://www.amazon.com/Automatic-Commercial-high-Pressure-Accessories-Restaurant/dp/B0868M9J9R, Mar. 23, 2020.

Hobart, Cleaning of Reusable Cups, Retrieved from: https://www.hobart-export.com/market-solutions/industry/cup-cleaning; Retrieved on: Sep. 23, 2021.

WebstaurantStore, Champion CG4 Low Temperature 48" Pass-Through Glass Washer, Left to Right—208/230V, Retrieved from: https://www.webstaurantstore.com/champion-cg4-low-temperature-48-pass-through-glass-washer-left-to-right-208-230v/253CG4LRV.html, Retrieved on: Sep. 23, 2021.

Northern Brewer, Vinator Bottle Rinser, Retrieved from: https://www.northernbrewer.com/products/vinator-bottle-rinser, Retrieved on Sep. 27, 2021.

Babymoov, Babymoov Turbo Pure Sterilizer & Dryer (2020), KiddiesKingdom.com, Retrieved from:https://www.kiddies-kingdom.com/health-hygiene/36070-babymoov-turbo-pure-sterilizer-dryer-2020.html, 2020.

Exair, High Efficiency Fixed Aluminum Air Amplifier, Inlet Dia.: 2.0 in, Grainger.com, Retrieved from: https://www.grainger.com/product/4LCX5?ef_id=EAlalQobChMlotPGscCI8gIVZGxvBB3KTQnjEAQYAyABEgJDjfD_BwE:G:s&s_kwcid=AL!2966!3!281698275816!!!g!469974894180!&gucid=N:N:PS:Paid, Retrieved on: Sep. 27, 2021.

(56) References Cited

OTHER PUBLICATIONS

Solvair, Food & Beverage, Retrieved from: https://www.solvair.co.uk/applications/food-and-beverage/; Retrieved on: Sep. 27, 2021.

Costway, Full-Automatic Washing Machine 7.7 lbs Washer, Retrieved from: https://www.walmart.com/ip/Full-Automatic-Washing-Machine-7-7-lbs-Washer-Spinner-Germicidal-UV-Light-Blue/354269146, Retrieved on Sep. 27, 2021.

KaTom, Perlick PKBR24 24" Underbar Glass Washer, Retrieved from: https://www.katom.com/199-PKBR24.html?gclid=EAlaIQobChMI_aLznJmE8gIV2wytBh3yjwltEAQYBSABEgLu_vD_BwE, Retrieved on Sep. 27, 2021.

Gosain, Gaurav, A More Sustainable Dishwasher, ME589: Sustainable Design, Dec. 16, 2013.

Dongguan Vistech Import & Export Co., Ltd, Mini UV Lamp Ultraviolet Germicidal Disinfection Lamp Portable UV Handheld Home Travel Ozone Sterilizer Light, Retrieved from: https://dgvistech.en.made-in-china.com/product/eZixUMaChJkH/China-Mini-UV-Lamp-Ultraviolet-Germicidal-Disinfection-Lamp-Portable-UV-Handheld-Home-Travel-Ozone-Sterilizer-Light.html, Retrieved on Sep. 30, 2021.

UVClean, UV-C Sanitizing Light Disinfection Telescoping Room Robot: Glow Trolley, Retrieved from: https://uvcleanhouse.com/products/glow-trolley, Retrieved on Sep. 30, 2021.

Meiko, Efficient Cleaning of Cups and Bottles, Retrieved from: https://www.meiko.info/en/efficient-cleaning-of-cups-and-bottles, Retrieved on Jan. 27, 2021.

Graf, Irina, United States Patent and Trademark Office, Notice of Allowance Issued in U.S. Appl. No. 17/490,894, 67 pages, dated Apr. 10, 2024.

Graf, Irina, United States Patent and Trademark Office, Notice of Allowance issued in U.S. Appl. No. 17/490,874, 21 pages, dated Mar. 5, 2024.

Graf, Irina, United States Patent and Trademark Office, Non-Final Office Action issued in U.S. Appl. No. 17/490,874, 145 pages, dated Sep. 13, 2023.

* cited by examiner

HIGH SPEED REUSABLE BEVERAGE CONTAINER WASHING SYSTEM WITH POP-UP ULTRAVIOLET SANITIZER

BACKGROUND

Due in part to the environmental concerns associated with disposable or single use beverage containers, many consumers are increasingly opting to use reusable cups, reusable bottles and other types of reusable beverage containers. In addition, some retail establishments, such as coffee shops, donut shops, and restaurants, have been willing to fill customer-provided cups and other beverage containers, and some have even introduced reusable cup programs where customers are able to purchase a reusable cup at a low initial cost when purchasing a beverage and then present that same cup at a later date for a refill.

While such programs have proven to be beneficial for both consumers and retail establishments, ensuring that the reusable cups are clean and sanitary prior to filling can be a challenge. Some municipalities, for example, have instituted ordinances that require a retail establishment to clean a work space after handling a customer-supplied reusable cup. Furthermore, pandemic-related concerns have led many retail establishments to discontinue the use of reusable cups due to the potential for a transmission of germs or contamination.

Retail establishments that serve beverages often use commercial-style dishwashers to wash cups and other utensils. Such dishwashers, however, are often configured to handle a large number of utensils in each load, and even the fastest dishwashers can still have runtimes of several minutes or more. Such dishwashers are also relatively large and noisy, and as a result are often placed in a kitchen or other area that is outside of the range of customers. As a result, traditional commercial-style dishwashers have a number of characteristics that make them generally unsuitable for use in connection with cleaning customer-provided reusable beverage containers.

Therefore, a significant need exists in the art for a system capable of washing reusable cups and other beverage containers in a fast and sanitary manner, and in particular, a system capable of being utilized in a retail establishment to clean customer-provided reusable beverage containers prior to filling, and to do so in a manner that is both fast and compatible with a fast-paced retail environment.

SUMMARY

The herein-described embodiments address these and other problems associated with the art by providing various improvements related to a beverage container washing system that may be used for rapid washing and/or sanitizing of beverage containers, e.g., for use in a retail environment to wash and/or sanitize customer-provided beverage containers prior to filling the beverage containers with purchased beverages, among other applications. Among other features, the beverage container washing system may include a pop-up ultraviolet sanitizer that may be used to sanitize an interior of a beverage container by extending into an opening of the beverage container and emitting ultraviolet light onto an interior surface of the beverage container.

Therefore, consistent with one aspect of the invention, an apparatus for washing a beverage container may include a housing defining a wash chamber, a holder disposed within the wash chamber and configured to hold the beverage container during a washing operation, a sprayer disposed in the wash chamber and including at least one nozzle, the at least one nozzle oriented to spray wash fluid onto the beverage container when the beverage container is held by the holder, and a pop-up ultraviolet sanitizer disposed in the wash chamber and including at least one ultraviolet light, the pop-up ultraviolet sanitizer configured to move between retracted and extended positions along an axis of extension thereof, where when in the extended position at least a portion of the pop-up ultraviolet sanitizer extends into an opening of the beverage container when the beverage container is held by the holder to emit ultraviolet light onto an interior surface of the beverage container.

In some embodiments, the sprayer includes a pop-up sprayer configured to rotate about an axis of rotation and to move between retracted and extended positions along the axis of rotation. Also, in some embodiments, the at least one nozzle includes an interior nozzle oriented to spray wash fluid into an interior of the beverage container when the beverage container is held by the holder and a lip nozzle oriented to spray wash fluid onto an outer lip of the beverage container when the beverage container is held by the holder.

Further, in some embodiments, the pop-up sprayer includes a manifold including an inlet configured to receive a wash fluid, an axial conduit extending generally along the axis of rotation, and a transverse conduit extending generally transverse to the axis of rotation, the axial and transverse conduits are in fluid communication with the inlet, the interior nozzle is in fluid communication with the inlet through the axial conduit and is axially offset from the inlet along the axis of rotation, and the lip nozzle is in fluid communication with the inlet through the transverse conduit and radially offset from the inlet relative to the axis of rotation.

In some embodiments, the lip nozzle is a first lip nozzle and the transverse conduit is a first transverse conduit, the manifold further includes a second transverse conduit extending generally transverse to the axis of rotation and angularly offset from the first transverse conduit, at least one nozzle further includes a second lip nozzle oriented to spray wash fluid onto the outer lip of the beverage container when the beverage container is held by the holder, the second lip nozzle in fluid communication with the inlet through the second transverse conduit and radially offset from the inlet relative to the axis of rotation, and the first and second transverse conduits are angularly offset from one another by about 180 degrees and extend substantially normal to the axis of rotation. In addition, in some embodiments, at least one of the first and second transverse conduits includes at least one drive nozzle configured to emit wash fluid in a tangential direction relative to the axis of rotation to drive rotation of the pop-up sprayer about the axis of rotation when spraying wash fluid from the pop-up sprayer.

In some embodiments, the pop-up ultraviolet sanitizer and the pop-up sprayer are disposed on a pop-up sprayer/ultraviolet sanitizer assembly. In addition, in some embodiments, the at least one ultraviolet light of the pop-up ultraviolet sanitizer is disposed on an end or side of the axial conduit. Moreover, in some embodiments, the at least one ultraviolet light of the pop-up ultraviolet sanitizer is disposed on the transverse conduit.

In some embodiments, the pop-up ultraviolet sanitizer and the pop-up sprayer are disposed on a pop-up sprayer/ultraviolet sanitizer assembly, and the axis of extension of the pop-up ultraviolet sanitizer and the axis of rotation of the pop-up sprayer are substantially coaxial with one another. Moreover, in some embodiments, the pop-up sprayer/ultraviolet sanitizer assembly includes a base, and the pop-up sprayer is supported by the base. In some embodiments, the pop-up sprayer is supported in a first sleeve in the base, and the pop-up ultraviolet sanitizer is supported in a second sleeve in the base. In addition, in some embodiments, the pop-up ultraviolet sanitizer and the pop-up sprayer are independently extendible from the base. In some embodiments, the pop-up ultraviolet sanitizer is supported by the pop-up sprayer in a sleeve in the pop-up sprayer, and a portion of an extension range of the pop-up ultraviolet sanitizer is provided by extension of the pop-up sprayer along the axis of rotation.

Moreover, in some embodiments, the pop-up ultraviolet sanitizer is separate from and adjacent to the sprayer. Also, in some embodiments, the sprayer includes a pop-up sprayer configured to rotate about an axis of rotation and to move between retracted and extended positions along the axis of rotation, and the axis of extension is parallel to and separated from the axis of rotation.

In some embodiments, the pop-up ultraviolet sanitizer is configured to rotate about the axis of extension and is supported by a base, and the pop-up ultraviolet sensor further includes a slip ring arrangement electrically coupling the pop-up ultraviolet sensor to the base to provide power to the at least one ultraviolet light.

In addition, in some embodiments, the pop-up ultraviolet sanitizer includes an extension mechanism configured to selectively extend the pop-up ultraviolet sanitizer. In some embodiments, the extension mechanism includes a stepper motor, a DC motor, a solenoid, a magnetic drive, a pneumatic drive, or a hydraulic drive.

Consistent with another aspect of the invention, a pop-up sprayer/ultraviolet sanitizer assembly for washing a beverage container disposed in a wash chamber may include a sprayer configured to rotate about an axis of rotation, the sprayer disposed in the wash chamber and including at least one nozzle, the at least one nozzle oriented to spray wash fluid onto the beverage container when the beverage container is positioned in the wash chamber, and at least one ultraviolet light. Each of the sprayer and the at least one ultraviolet light is configured to selectively extend along the axis of rotation of the sprayer, and when the sprayer is extended, the at least one nozzle is positioned to extend through an opening of the beverage container and spray wash fluid into an interior of the beverage container, and when the at least one ultraviolet light is extended, the at least one ultraviolet light is positioned to emit ultraviolet light onto an interior surface of the beverage container.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

DETAILED DESCRIPTION

Figure 1:
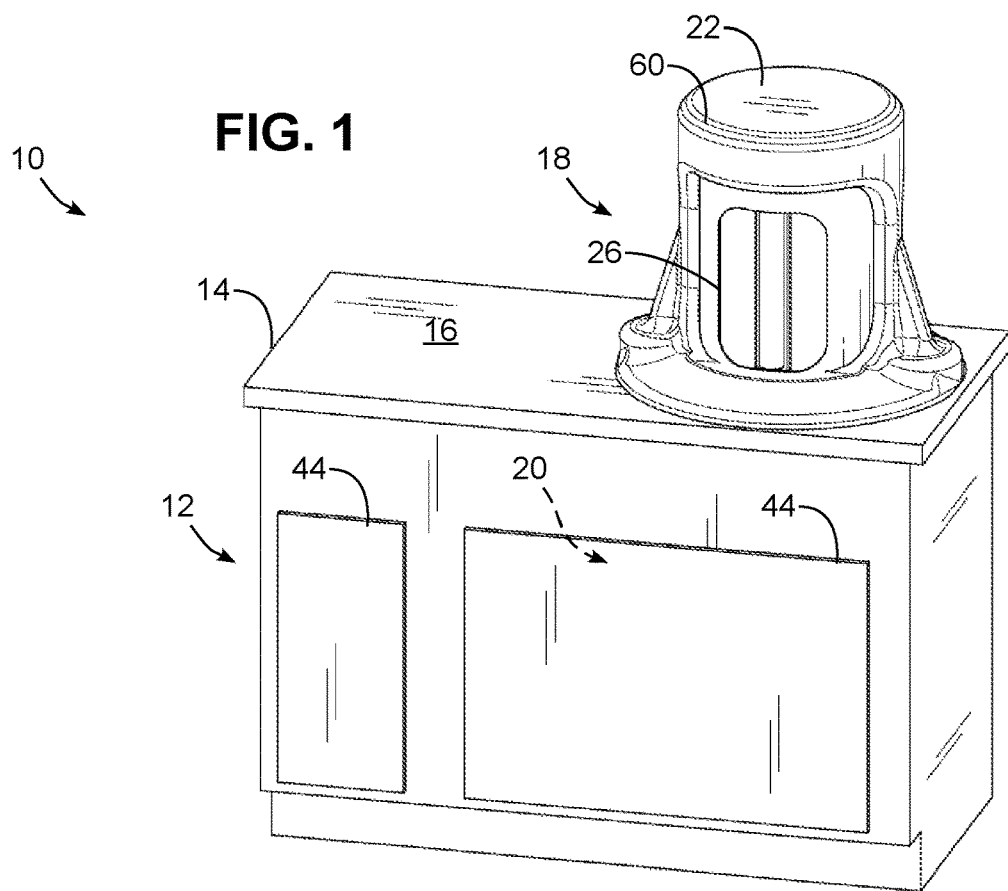
FIG. 1 is a perspective view of a beverage container washing system consistent with some embodiments of the invention.

In some embodiments consistent with the invention, a beverage container washing system may be used to rapidly wash beverage containers, including, for example, reusable beverage containers such as may be provided by customers of a retail establishment.

A beverage container, in this regard, may be considered to be any type of container that is capable of holding a beverage for consumption, including, for example, a cup, a bottle, a bowl, etc. A beverage container may generally include a mouth or opening defined by a lip, and may or may not include a cap, a lid or other form of closure. A beverage container may be reusable to the extent that the beverage container may be reused multiple times, in contrast with a disposable or single use beverage container that is generally thrown away after use.

A beverage container washing system consistent with some embodiments of the invention may be used to wash or clean a beverage container. In some embodiments, a beverage container washing system may also be considered to be a sanitizing system that is also capable of sanitizing a beverage container to inactivate, reduce or destroy microorganisms on one or more interior and/or exterior surfaces of the beverage container, e.g., bacteria and other pathogenic organisms. Sanitization may be achieved through the use of high temperatures, ultraviolet irradiation, disinfecting agents, or some combination of the same, such that a sanitizing operation may be considered to be a particular type of washing operation where some degree of sanitization occurs in addition to washing or cleaning. It will be appreciated, however, that some of the concepts disclosed herein may be utilized in connection with washing systems that, while capable of washing or cleaning a beverage container, are not considered to sanitize the beverage container to the extent required to consider the beverage container as being sanitized at the completion of a washing operation.

It will also be appreciated that a beverage container washing system consistent with the invention may be, but is not necessarily, used in a retail environment (e.g., a bar, a coffee shop, a restaurant, etc.) to rapidly wash the beverage container of a customer prior to filling the beverage container with a beverage that has been purchased by a customer, e.g., in some instances, less than one minute, and in some instances, about 30 seconds or less. Further, a beverage container washing system consistent with the invention may be, but is not necessarily, used to rapidly wash a single, individual beverage container in a washing operation. In other embodiments, for example, some of the concepts disclosed herein may be utilized in non-retail environments, including within a consumer's home, an office environment, or any other environment for which it may be desired to wash beverage containers. Further, even within a retail environment, a washing system consistent with the invention may be used in non-customer facing applications, e.g., behind the counter, in the kitchen, etc. Further, some of the concepts disclosed herein may be adapted for use in connection with washing multiple beverage containers in a single washing operation, as well as washing operations that take one or more minutes to complete.

In the example embodiment discussed hereinafter, hot water (e.g., about 150 degrees/65 degrees Celsius or higher in some embodiments, or about 165 degrees Fahrenheit/74 degrees Celsius or higher in some embodiments), high pressure (e.g., about 100 psi or greater), high speed air for drying, and ultraviolet irradiation are used to rapidly wash and sanitize an individual beverage container, e.g., in about 30 seconds, and do so in a manner that has a minimal countertop space presence. Furthermore, in order to minimize interaction between a customer and retail establishment employee, separate entrance and exit openings are used, such that the opening in which a customer inserts an unwashed beverage container into the system prior to performing a washing operation is different from the opening in which a retail establishment employee removes the washed beverage container at the completion of the washing operation. A washing system consistent with the invention may, in some instances, move the beverage container between multiple stations to perform different actions, and in some instances, operate on different beverage containers concurrently in different stations. In other instances, a washing system consistent with the invention may perform all of the actions associated with a washing operation while the beverage container is maintained in the same location. It will be appreciated, however, that in other embodiments, a washing system consistent with the invention may use the same opening for insertion and removal of a beverage container, and may operate on multiple beverage containers at the same time. Further, in some embodiments, lower temperatures and/or pressures may be used, and ultraviolet irradiation and/or drying may be omitted, or additional actions, such as the introduction of detergents, disinfecting agents, etc. may be used. Therefore, the invention is not limited to the specific embodiments disclosed herein.

Now turning to the drawings, wherein like parts are denoted by like numbers throughout the several views, FIG. 1 illustrates a beverage container washing system or apparatus 10 consistent with some embodiments of the invention, and suitable for installation, for example, in a cabinet 12 that forms a counter 14 in a retail establishment. In the illustrated embodiment, washing system 10 may also be considered to be a sanitizing system 10 due to the use of hot water and/or ultraviolet irradiation, so these terms may be used interchangeably. It will be appreciated, however, that the reference to a particular concept used in a sanitizing system or in connection with a sanitizing operation does not necessarily mean that the concept cannot also be used in washing system or in connection with washing operations that are not necessarily considered sufficient for full sanitization of a beverage container.

Additional details regarding beverage container washing system 10, includes various alternative holders, pop-up sprayers, ultraviolet sanitizing assemblies, housings, and operations that may be utilized in connection therewith, are discussed, for example, in U.S. patent application Ser. No. 17/490,874, filed on Sep. 30, 2021 by Boyer et al., which is incorporated by reference herein and assigned to the same assignee as the present application.

Counter 14 includes a countertop 16, and washing system 10 includes a countertop portion 18 that projects above countertop 16 and an undercounter portion 20 that is predominantly mounted within cabinet 12 to minimize the amount of countertop space occupied by countertop portion 18. In other embodiments, washing system 10 may be fully implemented in a countertop, standalone or undercounter configuration, so the invention is not limited to the particular combination of countertop and undercounter portions as illustrated herein. In some embodiments, the countertop portion may be fixed to a countertop, but he undercounter portion may be separated, or may be mounted on a cart to simplify installation and service.

Figure 2:
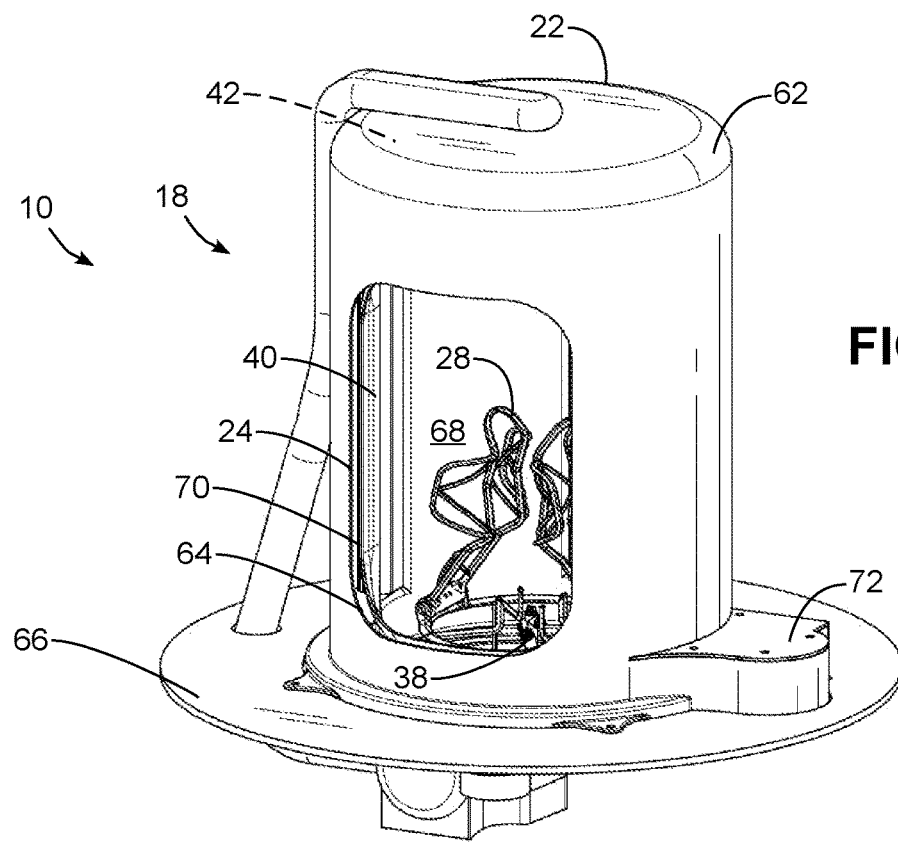
FIG. 2 is a perspective view of an opposite side of a countertop portion of the beverage container washing system of FIG. 1.

With additional reference to FIG. 2, which shows an opposite side of countertop portion 18 of washing system 10, the countertop portion 18 generally includes a housing 22 having a pair of openings 24, 26, with opening 24 operating as an entrance through which a beverage container is inserted or received prior to performing a washing operation and opening 26 operating as an exit through which a beverage container is accessed or removed after performing a washing operation. Through the use of separate openings 24, 26, handling of unwashed beverage containers by retail establishment employees may be reduced or eliminated. In other embodiments, however, a single entrance/exit opening may be used.

Countertop portion 18 also includes a holder 28 that is disposed within housing 22 and is configured to hold a beverage container during a washing or sanitizing operation. In addition, and with additional reference to FIG. 3, a number of assemblies 30, 32, 34 are also utilized for performing various actions on the beverage container during a washing or sanitizing operation, and are controlled by a controller 36, which will be discussed in greater detail below.

First, a spray assembly 30, including one or more sprayers (e.g., sprayer 38 as shown in FIG. 2) is disposed within housing 22 and configured to spray a wash fluid onto the beverage container while the beverage container is held by holder 28. The wash fluid may be water in some instances, while in other instances, the wash fluid may include various agents such as detergents, disinfecting agents, etc. As will become more apparent below, when sanitization is desired, the wash fluid sprayed by the spray assembly 30 may be heated to a sanitizing temperature, e.g., about 150 degrees Fahrenheit or higher in some embodiments, and about 165 degrees Fahrenheit or higher in some embodiments, and in some instances may be pressurized at a high pressure, e.g., about 100 psi or above. Second, an ultraviolet sanitizing assembly 32, including one or more ultraviolet lights 40 (one of which is shown in FIG. 2), is disposed within housing 22 and configured to emit ultraviolet light toward the beverage container while the beverage container is held by holder 28. In addition, as will become more apparent below, in some embodiments ultraviolet sanitizing assembly 32 may also include one or more pop-up ultraviolet sanitizers (not shown in FIG. 2) that may be extended into an interior of a beverage container to emit ultraviolet light into the interior of the beverage container. Third, a dryer assembly 34, e.g., including one or more air outlets 42, is disposed within housing 22 and configured to blow air onto the beverage container while the beverage container is held by holder 28. A number of other components in each of these assemblies, as noted above, may be disposed within cabinet 12, and may be accessed, for example, through one or more cabinet doors 44 (FIG. 1).

Figure 3:
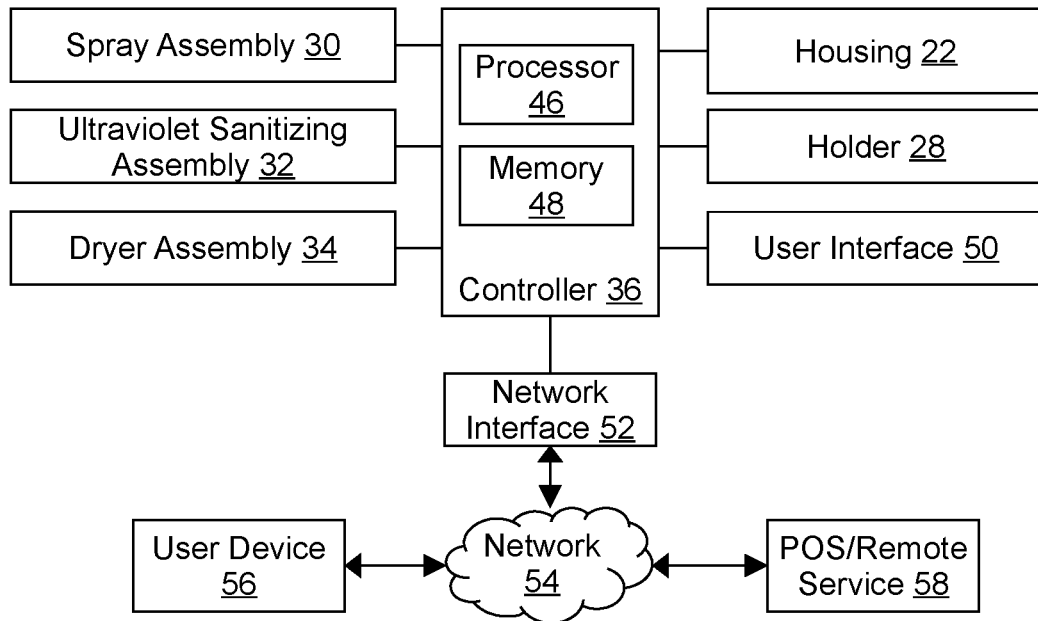
FIG. 3 is a block diagram of an example control system for the beverage container washing system of FIG. 1.

Now turning specifically to FIG. 3, washing system 10 may be under the control of a controller 36 that receives inputs from a number of components and drives a number of components in response thereto. Controller 36 may, for example, include one or more processors 46 and a memory 48 within which may be stored program code for execution by the one or more processors 46. The memory may be embedded in controller 36, but may also be considered to include volatile and/or non-volatile memories, cache memories, flash memories, programmable read-only memories, read-only memories, etc., as well as memory storage physically located elsewhere from controller 36, e.g., in a mass storage device or on a remote computer interfaced with controller 36. Controller 36 may also be implemented as a microcontroller in some embodiments, and as such these terms are used interchangeably herein. Controller 36 may also include discrete circuit logic in some embodiments, e.g., including passive and/or active circuit components.

As shown in FIG. 3, controller 36 may be interfaced with various components, including a spray assembly 30, ultraviolet sanitizing assembly 32 (including one or more ultraviolet lights configured to irradiate the exterior and/or interior surfaces of a beverage container), and dryer assembly 34, as well as housing 22 and/or holder 28. In addition, one or more user interfaces 50, e.g., including various input/output devices such as knobs, dials, sliders, switches, buttons, lights, textual and/or graphics displays, touch screen displays, speakers, image capture devices, microphones, etc., may be used for receiving input from and communicating with one or more users. Separate user controls and/or displays may be provided, for example, on or near housing 22 for a customer and a retail establishment employee (e.g., to start or stop a washing operation), and in some instances, additional controls and/or displays may be provided at different locations, e.g., under countertop 16 or behind a cabinet door 44, to perform additional operations, such as initializing and/or shutting off the system, flushing the system, displaying error conditions, etc.

In some embodiments, controller 36 may also be coupled to one or more network interfaces 52, e.g., for interfacing with external devices via wired and/or wireless networks 54 such as Ethernet, Bluetooth, NFC, cellular and other suitable networks. It may be desirable, for example, to interface with one or more user devices 56, e.g., a customer's mobile phone, to enable a customer to start a washing operation, in some instances in connection with ordering and/or paying for a beverage. It may also be desirable to interface with various backend devices such as a point of sale (POS) system and/or a remote service 58. Moreover, in some embodiments, at least a portion of controller 36 may be implemented externally, e.g., within a mobile device, a cloud computing environment, etc., such that at least a portion of the functionality described herein is implemented within the portion of the controller that is externally implemented.

In some embodiments, controller 36 may operate under the control of an operating system and may execute or otherwise rely upon various computer software applications, components, programs, objects, modules, data structures, etc. In addition, controller 36 may also incorporate hardware logic to implement some or all of the functionality disclosed herein. Further, in some embodiments, the sequences of operations performed by controller 36 to implement the embodiments disclosed herein may be implemented using program code including one or more instructions that are resident at various times in various memory and storage devices, and that, when read and executed by one or more hardware-based processors, perform the operations embodying desired functionality. Moreover, in some embodiments, such program code may be distributed as a program product in a variety of forms, and that the invention applies equally regardless of the particular type of computer readable media used to actually carry out the distribution, including, for example, non-transitory computer readable storage media. In addition, it will be appreciated that the various operations described herein may be combined, split, reordered, reversed, varied, omitted, parallelized and/or supplemented with other techniques known in the art, and therefore, the invention is not limited to the particular sequences of operations described herein.

As noted above, controller 36 may be interfaced in some embodiments with one or both of housing 22 and holder 28. In the embodiment illustrated in FIGS. 1-2, for example, washing system 10 includes a concentric housing arrangement, also referred to herein as a concentric dome arrangement, whereby housing 22 includes an outer decorative cover 60 coupled with a pair of concentric housing members or domes 62, 64 supported by a base 66. Concentric housing member or dome 62 is an outer concentric housing member or dome while concentric housing member or dome 64 is an inner concentric housing member or dome that is disposed inwardly from outer concentric housing member or dome 62 and forms at least a portion of a wash chamber 68 with the base. Entrance opening 24 and exit opening 26 are defined in outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation, a washing position where opening 70 is intermediate entrance and exit openings 24, 26 (thereby closing both openings), and an unloading position where opening 70 is aligned with exit opening 26 to provide access to the wash chamber for removal of the beverage container at the completion of a washing operation.

In other embodiments, however, no mechanical manipulation of a housing may be used, whereby controller 36 may not be electronically coupled to housing 22. For example, it may be desirable in some embodiments to keep an entrance opening and an exit opening open at all times, or to use a door or other manually or mechanically actuated closure.

In the illustrated embodiment of FIGS. 1 and 2, holder 28 may be fixed in location and thus no electronic coupling between controller 36 and holder 28 may be used. In other embodiments, however, it may be desirable to configure holder 28 to electronically open or close, rotate, and/or move, including moving between different stations, so controller 36 may be electronically coupled to holder 28 in some embodiments.

Figure 4:
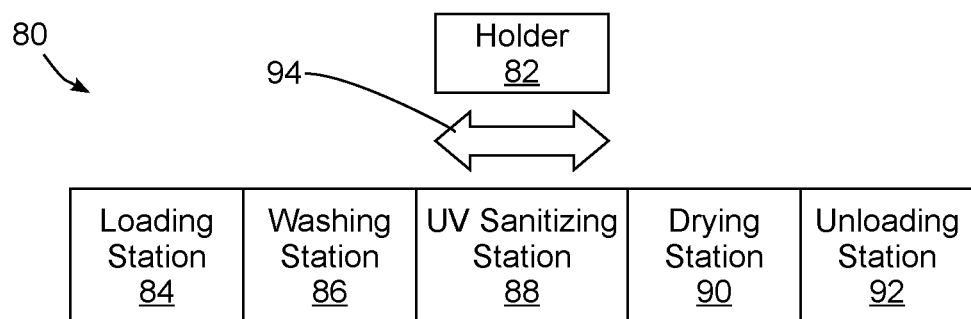
FIG. 4 is a block diagram of an alternate beverage container washing system to that of FIG. 1.

For example, as illustrated by washing system 80 of FIG. 4, a holder 82 may be moved between different stations, e.g., a loading station 84, a washing station 86, an ultraviolet sanitizing station 88, a drying station 90 and/or an unloading station 92, e.g., by a conveyor 94 or other articulating configuration. Further, in some embodiments, multiple actions may be performed at the same station (e.g., exposing to ultraviolet light while drying and/or washing in the same station), or multiple stations may perform different aspects of a particular action (e.g., separate wash and rinse stations).

Figure 5:
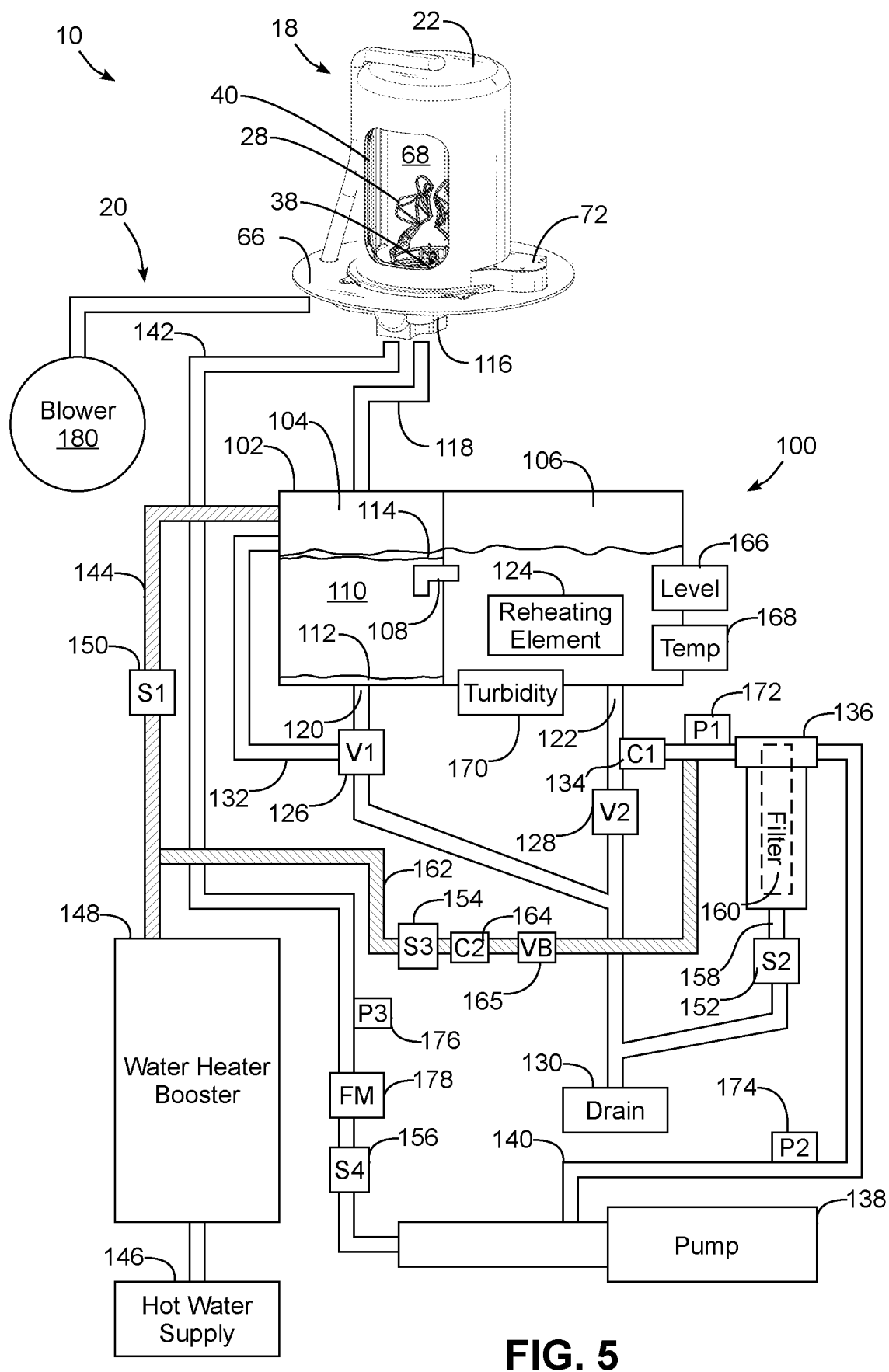
FIG. 5 is a block diagram of an undercounter portion of the beverage container washing system of FIG. 1.

Now turning to FIG. 5, and as discussed above, beverage container washing system 10 includes a number of additional components, many of which are in an undercounter portion 20, that operate each of spray assembly 30, ultraviolet sanitizing assembly 32 and dryer assembly 34. Spray assembly 30, for example, additionally includes a wash fluid recirculation assembly 100 that is disposed in cabinet 12 and underneath countertop 16 and is in fluid communication with sprayer 38 through countertop 16.

In particular, in the illustrated embodiment, it is desirable to recirculate wash fluid for use in multiple washing operations to reduce overall water and energy consumption. Rather than utilizing fresh water for each washing operation, the wash fluid may be reused for multiple washing operations, and in some instances, one or more fluid property sensors (e.g., a turbidity sensor and/or a conductivity sensor) may be used to monitor the state of the wash fluid and periodically perform a wash fluid refresh operation to drain at least a portion of the wash fluid to a drain and replace the removed portion with fresh water (referred to herein as make up water).

Wash fluid recirculation assembly 100, in particular, includes a tank 102 including first and second chambers 104, 106 with a cross-over 108 that fluidly couples first and second chambers 104, 106 to one another. First chamber 104 is generally used to house black water, while second chamber 106 is used to generally house grey water. Cross-over 108 may be implemented as an inverted conduit that is disposed below the fluid level of the wash fluid 110 disposed in tank 102, which generally reduces the amount of solid particles 112 (which generally fall to the bottom of first chamber 104 and thus below the inlet of the inverted conduit) and floating particles 114 (which generally float in first chamber 104 and thus above the inlet of the inverted conduit) that are drawn into second chamber 106. A collector 116 in base 66 of housing 22 collects wash fluid sprayed by sprayer 38, and the collected wash fluid is conveyed by a collector line 118 to first chamber 104 of tank 102.

Each chamber 104, 106 has an associated drain or outlet 120, 122, and tank 102 further includes a heater 124, e.g., a reheating element, that maintains the temperature of wash fluid 110 above the desired sanitizing temperature. Respective drain devices such as dump valves 126, 128 (also referred to as valves V1 and V2) are coupled to outlets 120, 122 and feed to a drain 130, e.g., in the building plumbing system. Dump valve 126 in some embodiments may also include an overflow line 132 to collect wash fluid when the fluid level rises above a predetermined level. In some embodiments, drain devices other than valves may be used in other embodiments, e.g., drain pumps, and in some embodiments, overflow may be controlled by a separate float that activates a drain pump.

A check valve 134 (also denoted as C1) is coupled between outlet 122 and dump valve 128 to route wash fluid to a filter 136 and then onward to a pump 138 through a recirculation line 140, and pump 138 pressurizes the wash fluid (e.g., to a pressure about 100 psi or above in some embodiments, and in some embodiments about 150 psi or above) and outputs the pressurized wash fluid to sprayer 38 through a sprayer supply line 142. In some embodiments, pump 138 may be a multi-stage pump, e.g., 1 hp, 17-stage pump. During a washing operation, wash fluid in the second chamber 106 of tank 102 is thus drawn out of outlet 122 and through filter 136 by pump 138, and then pressurized and supplied to sprayer 38 by pump 138. The wash fluid emitted by sprayer 38 is then collected in collector 116 of base 66 and returned to first chamber 104 of tank 102.

Fresh or make up water is supplied to tank 102 by a make up water line 144. In order to supply the fresh or make up water at a suitable temperature for washing or sanitizing operations, fresh water from a hot water supply 146 (e.g., output by a building water heater) may first be passed through a water heater booster 148, which maintains a quantity of water at an elevated temperature (e.g., about 150 degrees Fahrenheit or higher in some embodiments, and about 165 degrees Fahrenheit or higher in some embodiments). In other embodiments, however, fresh water may be supplied from a cold water supply and heated by water heater booster, and in some embodiments, water heater booster 148 may be omitted, with the temperature of the wash fluid in tank 102 predominantly controlled by reheating element 124.

Four additional valves, e.g., solenoid valves 150, 152, 154 and 156 (also denoted respectively as valves S1-S4), may also be incorporated into assembly 100. Valve 150 is a make up water valve, and is provided in make up water line 144 to control the supply of make up water to first chamber 104 of tank 102. Valve 156 is disposed in sprayer supply line 142, and is actuated when pump 138 is actuated to supply wash fluid to sprayer 38.

In addition, in the illustrated embodiment, filter 136 is a flushable filter and includes a second, cleanout outlet 158, and valve 152 is configured as a cleanout valve that couples cleanout outlet 158 to drain 130. Valve 154 in turn is configured as a filter clean valve that is coupled to make up water line 144 to supply fresh water to recirculation line 140 upstream of a filter element 160 of filter 136 through a fresh water supply line 162. It will be appreciated that when valves 152, 154 are closed and pump 138 is running wash fluid from tank 102 flows through an upstream portion of recirculation line 140, through filter element 160, and through the first outlet of the filter and a downstream portion of the recirculation line 140 to pump 138. However, whenever it is desirable to perform a filter cleaning operation (generally while pump 138 is shut off), valves 152 and 154 may be opened to supply fresh water to an outside or upstream side of the filter element 160 and then out cleanout outlet 158 to run fresh water over the outside of the filter element and flush any debris on the filter element into drain 130. In addition, in some embodiments, a check valve 164 (also denoted as C2) and a vacuum breaker 165 may also be provided in fresh water supply line 162 to inhibit reverse fluid flow to the make up water line 144. In other embodiments, gray water may be used to clean the filter, e.g., by coupling line 162 to an outlet of pump 138 instead of to a fresh water source, e.g., between pump 138 and valve 156, and with an additional valve controlling fluid flow through line 162.

Assembly 100 may also include a number of sensors to monitor the operation of the assembly and initiate various actions in response thereto. A fluid level sensor 166 may be disposed in tank 102 to sense a fluid level therein, and the controller may utilize the output of this sensor to control make up water valve 150 to maintain a desired fluid level in the tank. A temperature sensor 168 may be disposed in tank 102 to sense the wash fluid temperature, and the controller may utilize the output of this sensor to control reheating element 124 to regulate the wash fluid temperature in the tank. One or more fluid property sensors, e.g., a turbidity sensor 170, a conductivity sensor, and/or another sensor suitable for measuring various fluid properties, may also be disposed in tank 102, e.g., in second chamber 106, or otherwise disposed elsewhere in assembly 100, to sense the water quality and/or cleanliness of the wash fluid, and the controller may utilize the output of this sensor to trigger a wash fluid refresh operation that drains at least a portion of the wash fluid to drain 130 and adds fresh water to tank 102.

A pair of pressure sensors 172, 174 (also denoted as P1 and P2) may also be disposed upstream and downstream of filter element 160 (e.g., within upstream and downstream portions of recirculation line 140), and the controller may utilize the outputs of these sensors to sense a pressure differential indicative of a dirty or clogged filter element, and thereby trigger a filter cleaning operation. An additional pressure sensor 176 (also denoted as P3) and a flowmeter 178 may also be disposed downstream of pump 138, e.g., in sprayer supply line 142, and the controller may use the outputs of these sensors to monitor the supply of wash fluid to sprayer 38. As will also be discussed in greater detail below, a dryer assembly may also include one or more blowers, e.g., a blower 180, that supply air to one or more air knives.

Figure 6:
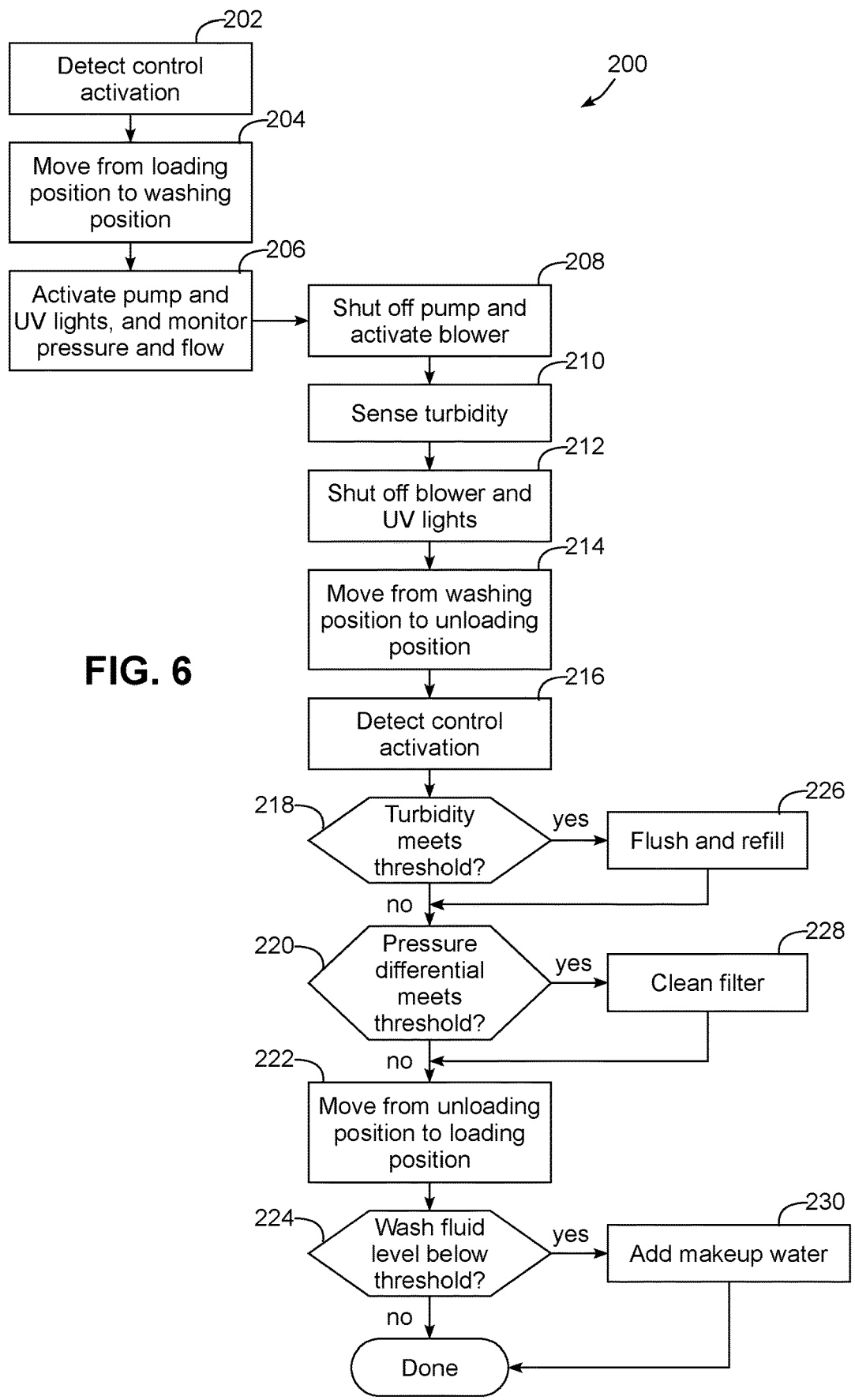
FIG. 6 is a flowchart illustrating an example sequence of operations for a washing operation performed by the beverage container washing system of FIG. 1.

FIG. 6 next illustrates an example sequence of operations 200 capable of being performed by controller 36 of beverage container washing system 10 to perform washing operations in a manner consistent with some embodiments of the invention. It is assumed that washing system 10 includes three positions, a loading position where the washing system is configured to allow a customer to insert a beverage container into the holder in the wash chamber (e.g., through entrance opening 24 of FIG. 2), a washing position where the washing system is configured to perform a washing operation (e.g., with entrance and exit openings 24, 26 closed), and an unloading position where the washing system is configured to allow an employee to remove a beverage container from the holder in the wash chamber (e.g., through exit opening 26 of FIG. 1). It is also assumed that at the beginning of sequence 200, the washing system 10 is in the loading position, and a customer has inserted a beverage container into the holder in the wash chamber. In addition, it will be appreciated that during this time, reheating element 124 (e.g., as a result of a background process executing in a controller, or in a dedicated circuit) may also be cycled to maintain the fluid temperature in the tank at a desired level.

Sequence 200 may be initiated, for example, in response to selection of a "start" control by a customer or employee, e.g., on a physical user interface provided on the washing system, via a foot pedal or switch, via a gesture or audible command, on a display of a POS system, on an app running on a mobile device, or another suitable manner for starting a washing operation. In block 202, activation of the control is detected, and in block 204, the washing system is moved from the loading position to the washing position (e.g., by rotating inner concentric housing member 64 with drive motor 72).

Next, in block 206, the pump of the spray assembly and the UV lights of the ultraviolet sanitizing assembly are activated to initiate spraying of the beverage container by sprayer 38 and irradiation of the beverage container with ultraviolet light (in another embodiment, the spray assembly and UV lights may be activated sequentially rather than concurrently). In addition, during this time pressure sensors 172-176 and flowmeter 178 are monitored to track the output flow of pump 138, as well as to monitor the pressure differential on the upstream and downstream sides of filter 136.

After some period of time, the pump is shut off and blower 180 of the dryer assembly is activated in block 208 to transition between washing the beverage container and drying the beverage container. Then, in block 210, the turbidity (or another property of the wash fluid) is sensed using sensor 170, and thereafter, the blower and UV lights are shut off in block 212, whereby the washing or sanitizing operation is complete.

Next, in block 214, the washing system is moved from the washing position to the unloading position (e.g., by rotating inner concentric housing member 64 with drive motor 72) to enable the beverage container to be removed from the holder in the wash chamber. Confirmation of removal of the beverage container is obtained in block 216 by detecting activation of an appropriate control (e.g., the same control used to start the washing operation in block 202 or a different control). Blocks 218 and 220 then determine whether conditions were detected indicating the need for either or both of a wash fluid refresh operation and a filter clean operation, and if neither operation is needed, control passes to block 222 to move the washing system from the unloading position to the loading position (e.g., by rotating inner concentric housing member 64 with drive motor 72) to prepare the washing system for a next washing operation. It will be appreciated that in embodiments where the loading and unloading positions are the same, block 222 may be omitted. Block 224 then determines, e.g., using fluid level sensor 166, whether the wash fluid level in the tank is below a threshold (e.g., where the wash fluid level has dropped below a minimum level), and assuming not, performance of sequence 200 is complete.

Returning to block 218, this block determines whether a need exists for a wash fluid refresh operation by determining if the turbidity sensed in block 210 (or another sensed fluid property) meets a threshold, e.g., where the turbidity of the wash fluid exceeds a level for which it is desired to flush at least a portion of the wash fluid from the tank and replace it with fresh water. If so, block 218 passes control to block 226 to perform a wash fluid refresh operation. In such an operation, one or both of dump valves 126 and 128 (or drain pumps, if used) may be actuated to drain at least a portion of the wash fluid in tank 102, and make up water valve 150 may be actuated to add make up water to the tank. In addition, during such an operation the filter may be cleaned concurrently with the flushing and refilling of wash fluid in some embodiments. Further, while in some embodiments a wash fluid refresh operation may replace all wash fluid with fresh water, in other embodiments only a portion of the wash fluid may be flushed and replaced with fresh water.

Returning to block 220, the block determines whether a need exists for a filter cleaning operation by determining if the pressure differential between pressure sensors 172, 174 meets a threshold, e.g., a pressure differential greater than some threshold that indicates that fluid flow through the filter has been impeded to an extent that cleaning of the filter is desirable. If so, block 220 passes control to block 228 to clean the filter, e.g., by actuating cleanout valve 152 and filter clean valve 154 to run fresh water over the outer surface of the filter element.

Returning to block 224, the block determines whether a need exists to add make up water to the tank by determining if the wash fluid level sensed by fluid level sensor 166 meets a threshold, e.g., is below a minimum fluid level. If so, block 224 passes control to block 230 to actuate make up water valve 150 to add makeup water, until the fluid level sensor indicates that the tank is full, whereby valve 150 may be shut off. In some embodiments, block 224 may be performed at the same time as blocks 218 and 220; however, it may be desirable to defer block 224 to allow for wash fluid in the wash chamber to have time to fully drain into the tank before checking the fluid level in the tank.

It will be appreciated that, assuming none of the supplemental operations of blocks 226, 228 and 230 are required, the bulk of the runtime of a washing operation is occupied by the washing, UV sanitizing and drying actions performed in blocks 206-212, and it will also be appreciated that the UV sanitizing action overlaps in time with each of the washing and drying actions, such that, for example, if the washing action takes X seconds and the drying action takes Y seconds, the UV sanitizing action takes Z=X+Y seconds. In other embodiments, particularly where a holder is moved between multiple stations, however, the UV sanitizing action may overlap only a portion of one or both of the washing and drying actions, or may not overlap with either of the washing and drying actions at all. In addition, it will be appreciated that moving between the loading, washing, and unloading positions may also occupy some time within a washing operation in some embodiments. It may be desirable in some embodiments, for example, to provide a washing operation having a duration of about 45 seconds or less, with, for example, about 5 seconds used to move from the loading position to the washing position, about 30 seconds for the washing action, about 5 seconds for the drying action, about 30 seconds for the UV sanitizing action (concurrent with the washing action, or alternatively in another embodiment about 35 seconds concurrently with both the washing and drying actions), and about 5 seconds to move from the washing position to the unloading position.

It will be appreciated that washing system 10 may vary in other embodiments in a number of manners. For example, an additional filter may be used in first chamber 104 of tank 102 in some embodiments to filter wash fluid before it is transferred to second chamber 106. Further, in some embodiments, a separate rinse action may be performed using a source of fresh water after the washing action. Further, in some embodiments, one or more disinfecting agents, e.g., various hypochlorite sanitizing compositions, may be introduced into tank 102 and maintained at a minimum level based upon sensing by a suitable sensor. In addition, further operations, such as startup operations that initialize the washing system, and shutdown operations that flush the washing system and shut down all components, may also be supported.

Concentric Housing Members

As noted above, while in some embodiments a holder may be movable between a plurality of stations during a washing operation, in other embodiments it may be desirable to utilize a holder that maintains the beverage container in a single location while various actions associated with a washing operation (e.g., loading, unloading, washing, rinsing, UV sanitization and/or drying) are performed. Furthermore, while in some embodiments a beverage container may be inserted into and removed from a beverage container washing system through a single opening, in other embodiments it may be desirable to utilize a housing configuration that enables a beverage container to be inserted into a washing system and removed from the washing system through separate openings, e.g., in a retail environment such that a customer may insert an unwashed beverage container into one side of a washing system built into or supported on a retail counter and an employee may remove the beverage container from the other side of the washing system after washing is complete, thereby minimizing employee contact with unwashed customer beverage containers.

To address these concerns, it may be desirable to utilize a washing system design that incorporates a pair of concentric housing members that are supported on a base, with an inner one of the concentric housing members being disposed inwardly from the outer one of the concentric housing members and forming at least a portion of a wash chamber, and with each of the concentric housing members including an opening. At least one of the concentric housing members may also be rotatable about an axis of rotation, e.g., under the control of a drive assembly, to selectively align the respective openings in the inner and outer concentric housing members to either enable or inhibit access to the wash chamber, e.g., to enable a user to insert or remove a beverage container into or from a holder disposed in the wash chamber when the openings are aligned, or to restrict external access to the holder in the wash chamber during the washing operation, and in some instances, prevent any wash fluid sprayed in the wash chamber during the washing operation from escaping from the washing system.

In some instances, the axis of rotation may be vertical, and moreover, in some instances, multiple openings may be provided in either or both of the inner and outer concentric housing members to provide different points of access to the wash chamber (e.g., to provide separate openings for a customer and an employee, or otherwise provide separate openings on different sides of a washing system). Further, while in some embodiments, only a single concentric housing member may be rotatable, with the other concentric housing member remaining fixed or stationary, in other embodiments, both concentric housing members may be rotatable.

Beverage container washing system 10 of FIGS. 1-2 illustrates such a concentric housing member arrangement, where concentric housing member 62 and outer concentric housing member 64 are configured as concentric domes that are generally dome shaped and have generally cylindrical sidewalls. It will be appreciated, however, that the concentric housing members can have a wide variety of alternate shapes, sizes and configurations, so the invention is not limited to the concentric dome configuration illustrated herein. As one example, in one embodiment an inner concentric housing member may have an open-top, e.g., configured as a cylinder, such that the top of the wash chamber is defined at least in part by the outer concentric housing member. By doing so, drying, spraying and/or ultraviolet sanitization actions may be performed at least in part by stationary components operating from an overhead position and not requiring electrical or other connections to a movable concentric housing member.

Figure 7:
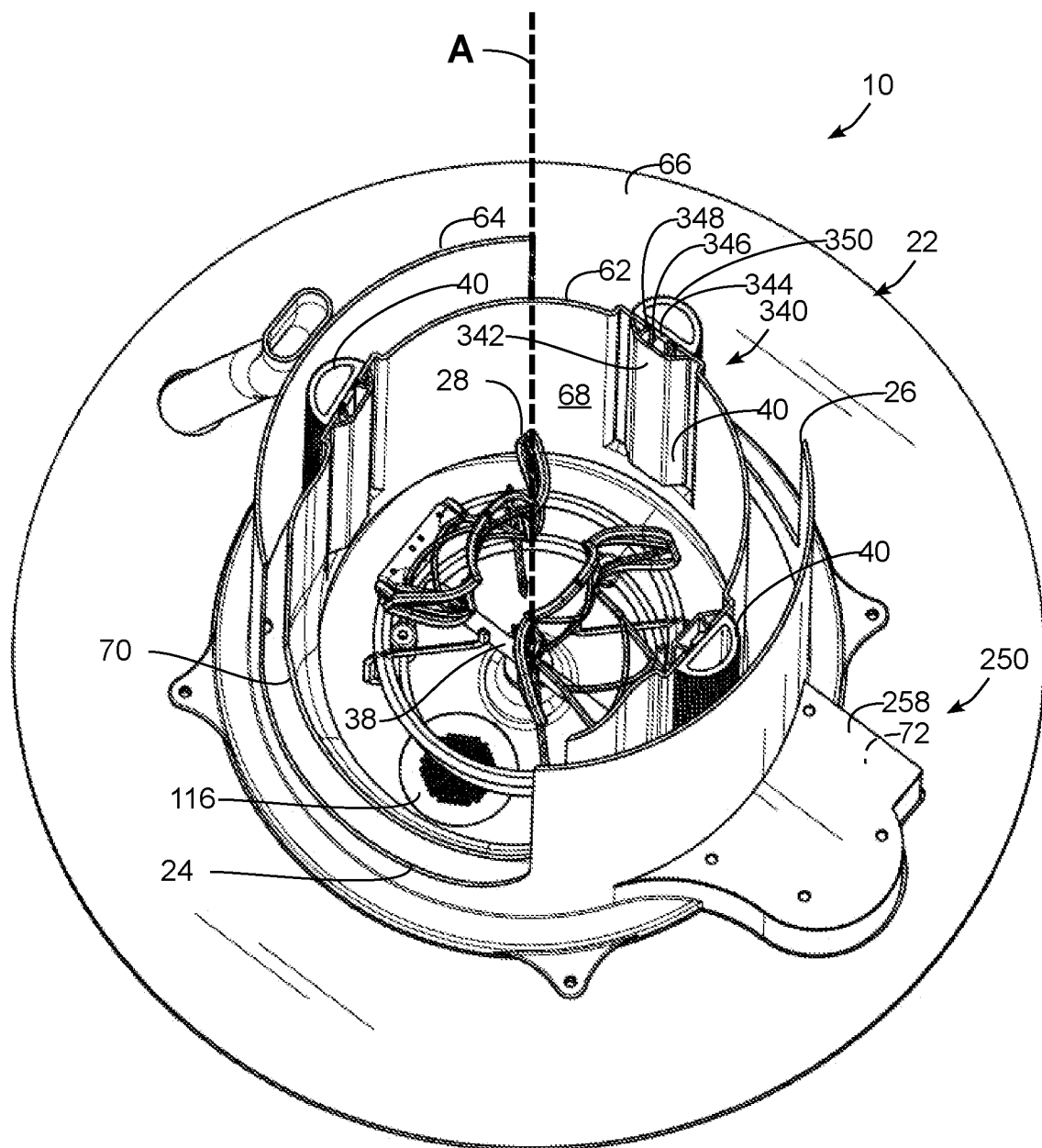
FIGS. 7-9 are cross-sectional views taken through the countertop portion of the beverage container washing system of FIG. 1 in respective loading, washing and unloading configurations.
Figure 8:
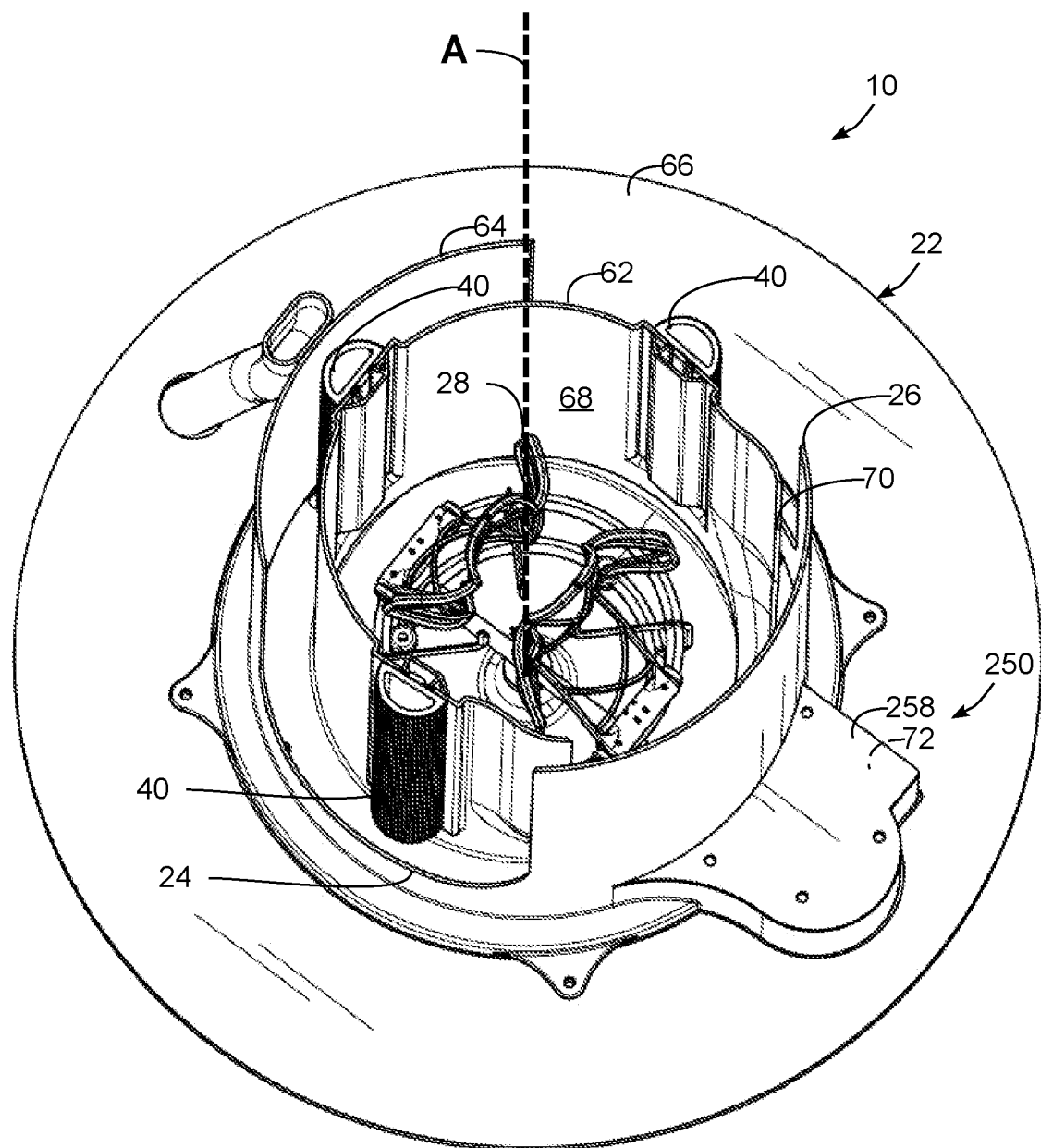
Figure 9:
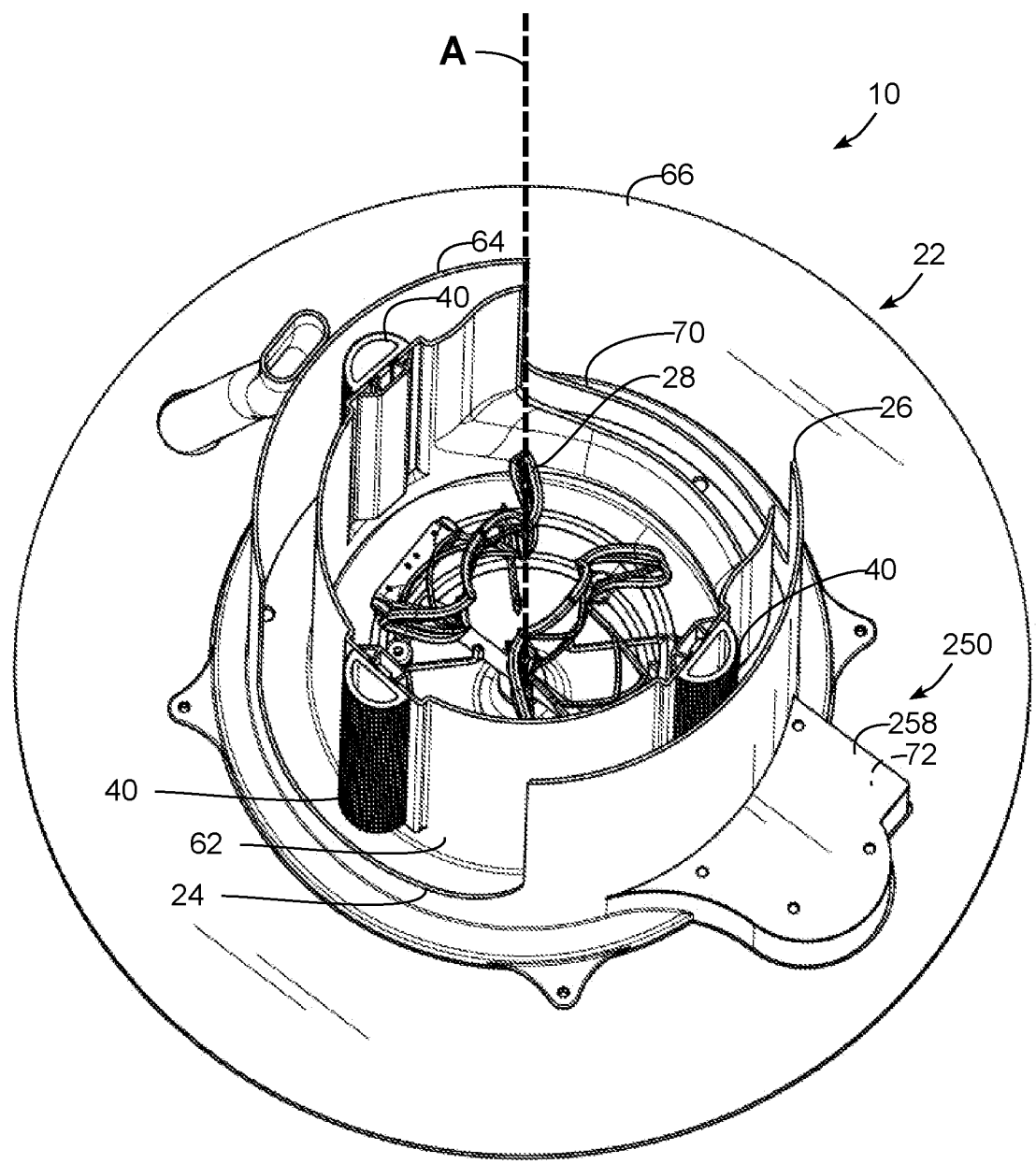

With further reference to FIGS. 7-9, each concentric housing member 62, 64 fully circumscribes an axis of rotation A, and among the concentric housing members 62, 64, inner concentric housing member 62 is rotatable while outer concentric housing member 64 is fixed or stationary. An entrance opening 24 and exit opening 26 are defined on opposite sides of outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation (FIG. 7), a washing position where opening 70 is intermediate entrance and exit openings 24, 26 (thereby effectively closing both openings as shown in FIG. 8), and an unloading position where opening 70 is aligned with exit opening 26 to provide access to the wash chamber for removal of the beverage container at the completion of a washing operation (FIG. 9). The loading, washing and unloading positions represent different relative positions between the two concentric housing members 62, 64.

It will be appreciated that in some embodiments, the mere alignment or misalignment of opening 70 and entrance and exit openings 24, 26 may be sufficient to inhibit the escape of wash fluid from wash chamber 68. It should also be noted that opening 70 as illustrated in the figures does project radially from the inner cylindrical wall defining the wash chamber such that an edge of opening 70 may touch or at least define a reduced gap between opening 70 and the inner cylindrical wall of outer concentric housing member 64. In other embodiments, however, it may be desirable to also include a sealing arrangement on one or both of concentric housing members 62, 64 (e.g., around one or more of openings 24, 26 and 70) to further inhibit the escape of wash fluid from wash chamber 68.

Figure 10:
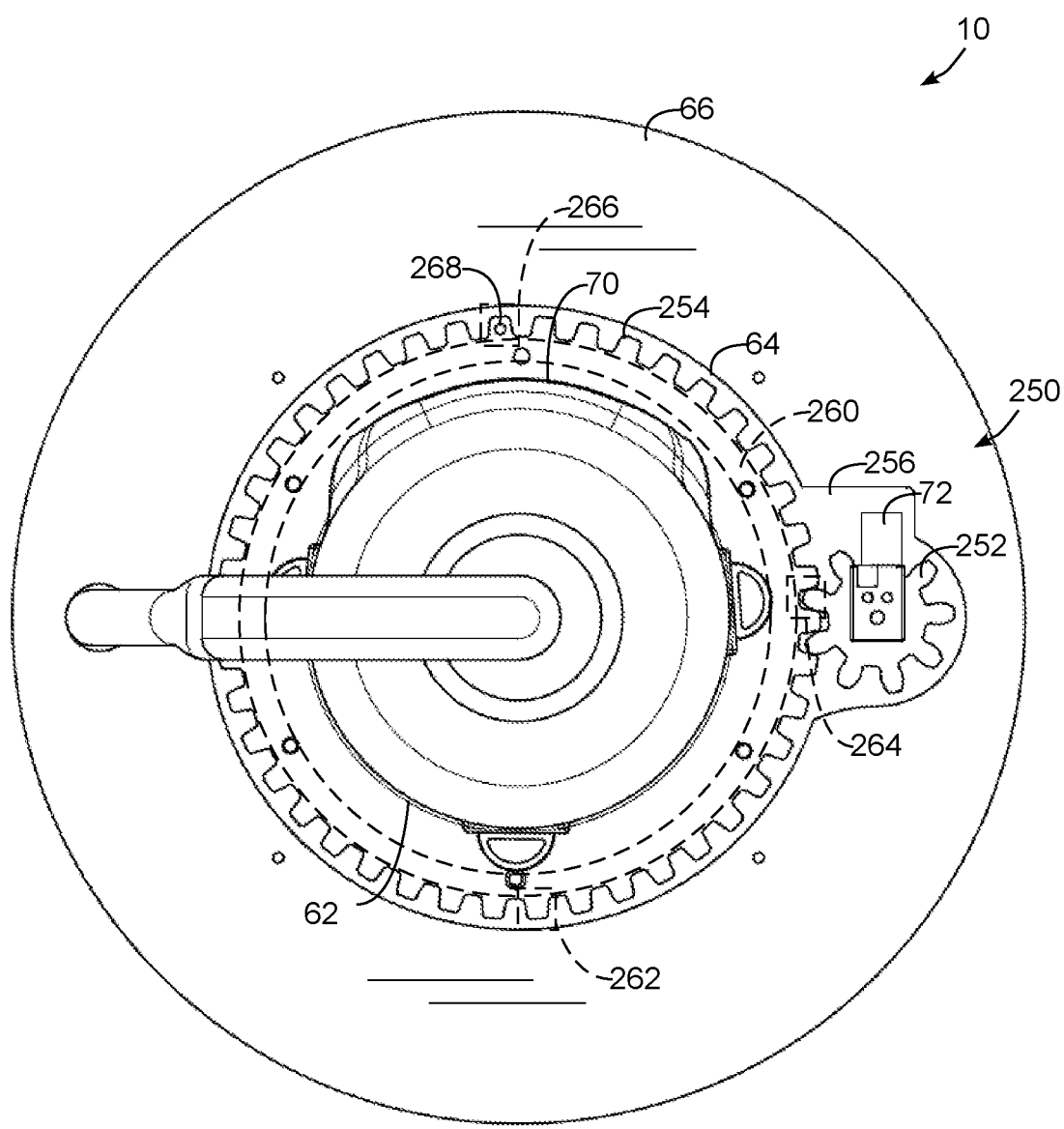
FIG. 10 is a partial top plan view of the beverage container washing system of FIG. 1, with portions thereof removed to illustrate a housing drive system thereof.

With additional reference to FIG. 10, drive motor 72 may be incorporated into a drive assembly 250 that further includes a pair of gears 252, 254 configured to drive rotation of inner concentric housing member 62 with drive motor 72. Drive motor 72 may be an electric, e.g. a DC motor, and drive motor 72 and gear 252 may be disposed in a compartment 256 formed in outer concentric housing member 64, and may be accessed through a cover 258. Gear 254 may be coupled to inner concentric housing member 62, and in some embodiments, may circumscribe the perimeter of the inner concentric housing member. In some embodiments, gear 254 may also be formed integrally with inner concentric housing member 62. In another embodiment, gear 254 may be formed as an internal ring gear and may be driven from a point inward from inner concentric housing member 62. Inner concentric housing member 62 may be rotatably supported on a turntable bearing 260. In other embodiments, other drive assembly configurations may be used to drive rotation of inner concentric housing member 62, e.g., a friction wheel drive assembly, a belt or chain drive, a piston or linear motor drive, etc. Particularly where rotation is limited to only about 90 degrees, as may be the case when two openings are provided in inner concentric housing member 62, various mechanical arrangements, including linear drives, may be used to impart sufficient rotation to the inner concentric housing member.

Furthermore, in order to controllably rotate inner concentric housing member 62 between the different relative positions, a position detector, e.g., an encoder or other suitable position sensor, may be used. In one embodiment, for example, a position detector may be implemented by a set of stationary three reed switches 262, 264, 266 configured to sense a magnet 268 coupled to inner concentric housing member 62 when the opening 70 is in each of the loading, washing and unloading positions. Other position detector configurations may be used in other embodiments, however, so it will be appreciated that the invention is not limited to the particular configuration illustrated in FIG. 10.

Dryer Assembly

As noted above in connection with FIGS. 1-2, it may also be desirable in some embodiments to incorporate a dryer assembly in a beverage container washing system, e.g., to blow off any standing wash fluid, water or other moisture left on the beverage container subsequent to spraying by a spraying assembly. It will be appreciated, however, that where the housing of the beverage container washing system incorporates movable components, supplying a flow air to the beverage container can be complicated by the need to supply the air in a manner that accommodates the movable components.

In the specific case of beverage container washing system 10, which incorporates a rotatable inner concentric housing member 62, for example, it is generally desirable to provide a flow of air to wash chamber 68, but do so in a manner that accommodates the rotatable nature of inner concentric housing member 62.

Figure 11:
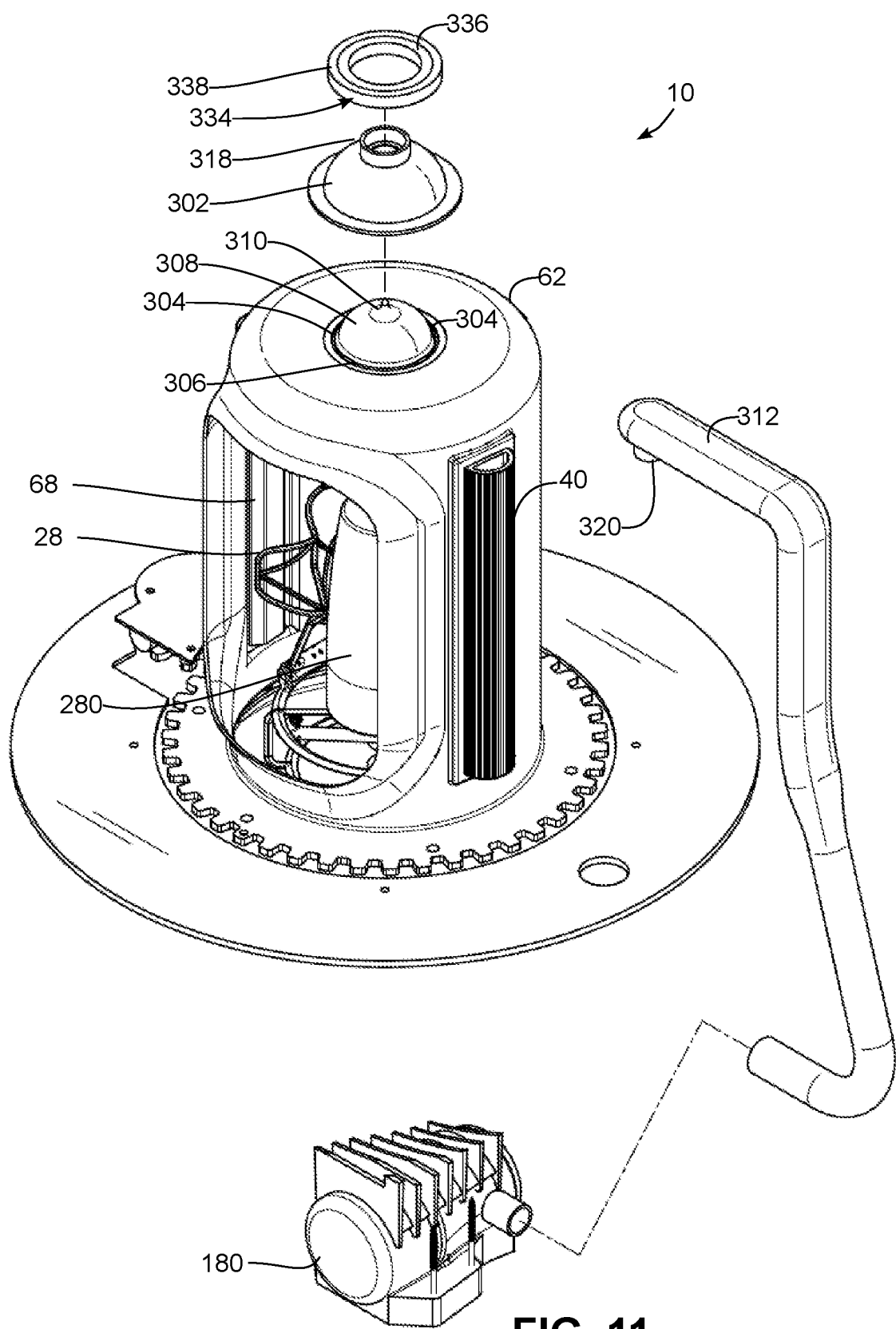
FIG. 11 is an exploded top perspective view of dryer assembly and ultraviolet sanitizing assembly components of the beverage container washing system of FIG. 1.
Figure 12:
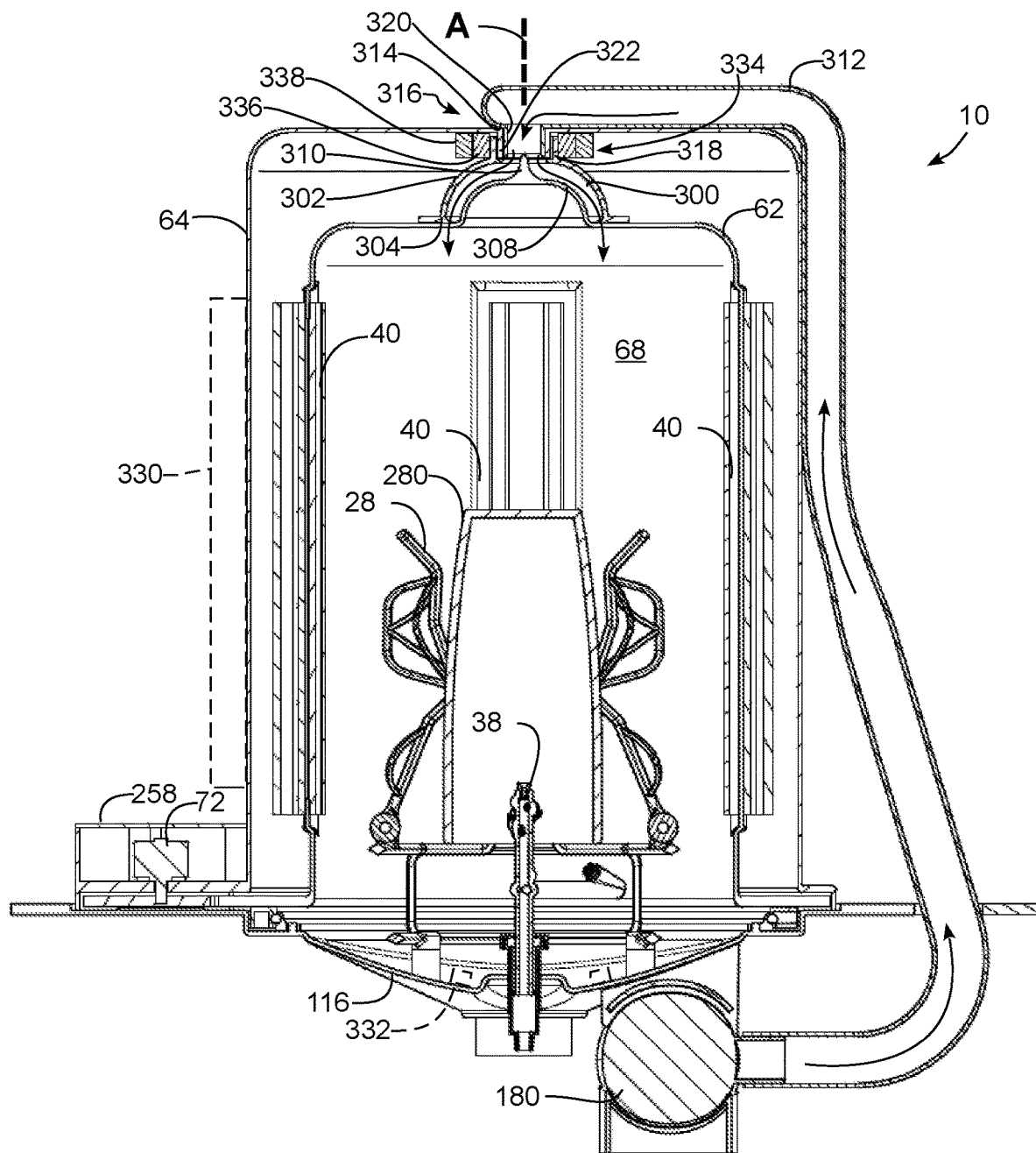
FIG. 12 is a side cross-sectional view of dryer assembly and ultraviolet sanitizing assembly components of the beverage container washing system of FIG. 1.

In the illustrated embodiment, and with further reference to FIGS. 11-12 (note that outer concentric housing member 64 has been omitted from FIG. 11), a dryer assembly may include an air knife chamber 300 disposed proximate a top of inner concentric housing member 62. Air knife chamber 300 is defined in part by an outer shell 302, which, in some embodiments, may be integrally molded or formed with inner concentric housing member 62, while in other embodiments, may be welded, fastened, or otherwise secured to a wall of inner concentric housing member 62 such that the outer shell 302 covers at least a portion of the wall of the inner concentric housing member. In the illustrated embodiment, outer shell 302 and air knife chamber 300 are configured to rotate with the inner concentric housing member, while in other embodiments, outer shell 302 and air knife chamber 300 may be stationary, such that inner concentric housing member 62 rotates relative to the outer shell and the air knife chamber.

One or more air knife openings 304 are defined in inner concentric housing member and are in fluid communication with air knife chamber 300 to direct a flow of air toward a beverage container 280 while the beverage container is held by holder 28 in wash chamber 68. In the illustrated embodiment, for example, an annular arrangement of four radially-offset and arcuate air knife openings 304 (which at least partially circumscribe the axis of rotation A) are used, which are separated from one another by four tabs 306 that support a central hub 308 having a central nipple 310. As seen in FIG. 12, the shape of central hub 308 and central nipple 310 serves to distribute air flow radially outwardly to the air knife openings 304 that are radially-offset from the axis of rotation A. Moreover, in the illustrated embodiment, central nipple is upwardly-facing and axially aligned with the axis of rotation A.

Air is suppled to air knife chamber 300 from a stationary air supply conduit 312 that is in fluid communication with blower 180 to receive a supply of pressurized air. In the illustrated embodiment, at least a portion of conduit 312 extends substantially vertically along a side of outer concentric housing member 64, around a top side of outer concentric housing member 64, and then through an opening 314 formed in the top side of outer concentric housing member 64.

Air knife chamber 300 is in fluid communication with stationary air supply conduit 312 through a rotary seal 316, which in the illustrated embodiment is formed by a three concentric tubes 318, 320, 322 that are all axially aligned with the axis of rotation A. Concentric tube 318 is an upwardly-facing tube that defines an air inlet for air knife chamber 300, while concentric tube 320 is a downwardly-facing tube that extends downwardly from stationary air supply conduit 312 and forms an air outlet therefor. Concentric tube 322 is also downwardly-facing, but extends downwardly from outer concentric housing member 64 and defines opening 314. In the illustrated embodiment, concentric tube 322 is inward of concentric tube 318, and concentric tube 320 is inward of concentric tube 322, with at least portions of all three concentric tubes overlapping with one another to form the rotary seal. Moreover, in some embodiments, rotary seal 316 also functions as an axle for rotation of inner concentric housing member 62 to rotate about axis of rotation A. As such, air from stationary air supply conduit 312 may be provided to wash chamber 68 through rotating concentric housing member 62.

It will be appreciated that other rotary seals may be used in other embodiments, so the invention is not limited to the concentric tube arrangement illustrated in FIGS. 11-12. Moreover, it will be appreciated that a wide variety of alternate numbers and configurations of air knife openings may be used in other embodiments, e.g., to direct air in multiple directions and at other regions of a beverage container, including, in some embodiments, an interior of the beverage container. Additional stationary air knife openings may also be used in some embodiments, e.g., directed upwardly from base 66, and in some embodiments, no movable air knives may be used, or drying may not be supported whatsoever in a cup washing system. Where an inner concentric housing member has an open top, as another example, stationary air knives may be used in lieu of the configuration illustrated in FIGS. 11-12. Further, air knife openings may be configured in other manners in other embodiments, e.g., using nozzles capable of controlling direction, flow rate and/or spray pattern, as will be appreciated by those of ordinary skill in the art having the benefit of the instant disclosure.

Ultraviolet Sanitizing Assembly

As also noted above in connection with FIGS. 1-2, it may also be desirable in some embodiments to incorporate an ultraviolet sanitizing assembly in a beverage container washing system, e.g., to sanitize an outer/exterior and/or inner/interior surfaces of a beverage container by irradiating with ultraviolet light. It will be appreciated, however, that where ultraviolet lights are supported on movable components, e.g., movable housing components, supplying power to ultraviolet lights mounted to such movable components can be complicated by the need to supply the power in a manner that accommodates the movable components. In the specific case of beverage container washing system 10, which incorporates a rotatable inner concentric housing member 62, for example, it may be desirable to provide one or more ultraviolet lights 40 within wash chamber 68 to emit ultraviolet light onto the exterior surfaces of a beverage container, but do so in a manner that accommodates the rotatable nature of inner concentric housing member 62.

Ultraviolet sanitizing lights, which are generally formed by arrays of ultraviolet (UV) light emitting diodes (LEDs), or alternatively by other devices capable of emitting ultraviolet light (e.g., incandescent or halogen lights), are susceptible to being attenuated by materials lacking sufficient transmissivity to ultraviolet wavelengths, and in some instances, UV LEDs may require special materials that offer a unique transmissivity, as the UV light may be attenuated even by some visually translucent materials. As such, it may be desirable in some embodiments to avoid the high cost of creating large parts that are UV light transmissive by restricting the amount of material between the UV LEDs and the beverage container to be sanitized. In the illustrated embodiment, therefore, incorporating UV LEDs into the inner concentric housing member 62 may reduce potential transmissivity issues, and may even allow for the inner concentric housing member 62 to be formed from a material that is translucent or transparent to visible light but that is more opaque to ultraviolet light. Various materials that may be used in some embodiments are polycarbonate, acrylic, standard Glass, etc., although other materials may be used. In some instances, this may even provide a pleasing visual effect for users, as the visual light emitted by the UV LEDs may be visible through the inner (and outer, if formed of a similar material) concentric housing member 62, while still blocking user exposure to ultraviolet wavelengths.

In the illustrated embodiment, and with continuing reference to FIGS. 11-12 (note that outer concentric housing member 64 has been omitted from FIG. 11), an ultraviolet sanitizing assembly may include one or more ultraviolet lights 40 that are coupled to a rotatable concentric housing member, in this case inner concentric housing member 62. As noted above, while ultraviolet lights 40 may be implemented using one or more UV LEDs, in other embodiments, other devices capable of emitting ultraviolet light (e.g., incandescent or halogen lights) may also be used. In other embodiments, e.g., where an outer concentric housing member is rotatable, one or more ultraviolet lights may be mounted to an outer concentric housing member. Further, in some embodiments, additional ultraviolet lights may be located in fixed or stationary locations, e.g., as illustrated in FIG. 12 by ultraviolet light 330 on outer concentric housing member 64, as illustrated in FIG. 12 by ultraviolet light 332 in collector 116, or in other locations such as the space between concentric housing members 62, 64.

It should be noted that in some embodiments ultraviolet light 330 may be positioned on outer concentric housing member 64 such that opening 70 of inner concentric housing member 62 faces ultraviolet light 330 when in the washing position, such that three ultraviolet lights 40 may be disposed on inner concentric housing member 62, and with all four ultraviolet lights 40, 330 evenly spaced in 90 degree increments about the axis of rotation to provide relatively full coverage of the outer or exterior surface of beverage container 280. It should also be noted that some ultraviolet lights, e.g., ultraviolet light 332, may be positioned to irradiate an inner surface of beverage container 280. In addition, as will be discussed in greater detail below, a pop-up ultraviolet sanitizer may also be incorporated into an ultraviolet sanitizing assembly in some embodiments to selectively extend into an interior of a beverage container to position an ultraviolet light closer to the interior of the beverage container to expose one or more interior surfaces of the beverage container to ultraviolet light.

In order to power ultraviolet lights 40, a slip ring 334 may be coupled between inner and outer concentric housing members 62, 64, with, for example, a rotatable portion 336 coupled to inner concentric housing member 62 and a stationary portion coupled to outer concentric housing member 64. Slip ring 334 may utilize various electromechanical constructions, including rotary electrical contacts, commutators, rotary transformers, rotary unions, pancake slip rings, wireless slip rings, etc., and wiring harnesses (not shown) both on the stationary and rotatable sides of the slip ring may be used to route the electrical power to each ultraviolet light 40. Further, slip ring 334 may be positioned elsewhere within housing 22, e.g., along the top or side wall of inner concentric housing member 62, at the base of inner concentric housing member 62, etc.

Various ultraviolet light constructions may be used for ultraviolet lights 40 in different embodiments. In the illustrated embodiment, for example, each ultraviolet light 40 may extend substantially vertically along a side wall of inner concentric housing member 62, and in some instances, and as best illustrated in FIGS. 7-9, the inner concentric housing member 62 may include a substantially vertical mounting arrangement 340 configured to receive each ultraviolet light 40.

The mounting arrangement 340 in some embodiments may include an ultraviolet transmissive cover 342 that overlays ultraviolet light 40 to permit ultraviolet light transmission into wash chamber 68, and that further seals the ultraviolet light from the wash chamber. In some instances, the cover 342 may be mounted, welded or otherwise secured to inner concentric housing member 62, while in other instances, the cover may be integrally molded thereto. In either instance, it is generally desirable for the other walls of inner concentric housing member 62 to be formed of an ultraviolet blocking material that inhibits ultraviolet light transmission through the walls of inner concentric housing member 62.

The mounting arrangement may 340 may also include one or more openings 344 formed in a wall of inner concentric housing member 62 and aligned with a plurality of UV LEDs 346 disposed on a circuit board 348. By doing so, circuit board 348 may be positioned on an outer surface of inner concentric housing member 62, with the UV LEDs 346 positioned to emit ultraviolet light through openings 344. In addition, in some embodiments, it may also be desirable to incorporate a heat sink 350, which may run along a portion or the entire length of circuit board 348 and be thermally coupled thereto, and serve to further seal the circuit board from the surrounding environment.

It will be appreciated that different numbers and/or orientations of ultraviolet lights may be used in other embodiments, e.g., two ultraviolet lights having respective angular positions about the axis of rotation A spaced about 90 to about 180 degrees, or less, from one another, three ultraviolet lights having respective angular positions about the axis of rotation A spaced about 90 to about 120 degrees from one another, four ultraviolet lights having respective angular positions about the axis of rotation A spaced about 90 degrees or less from one another, etc. In one example embodiment, for example, two opposing ultraviolet lights may be supported on inner concentric housing member 62 and two opposing ultraviolet lights may be supported on outer concentric housing member 64 such that ultraviolet lights are oriented in 90 degree increments when the inner concentric housing member 62 is in the washing position.

Figure 13:
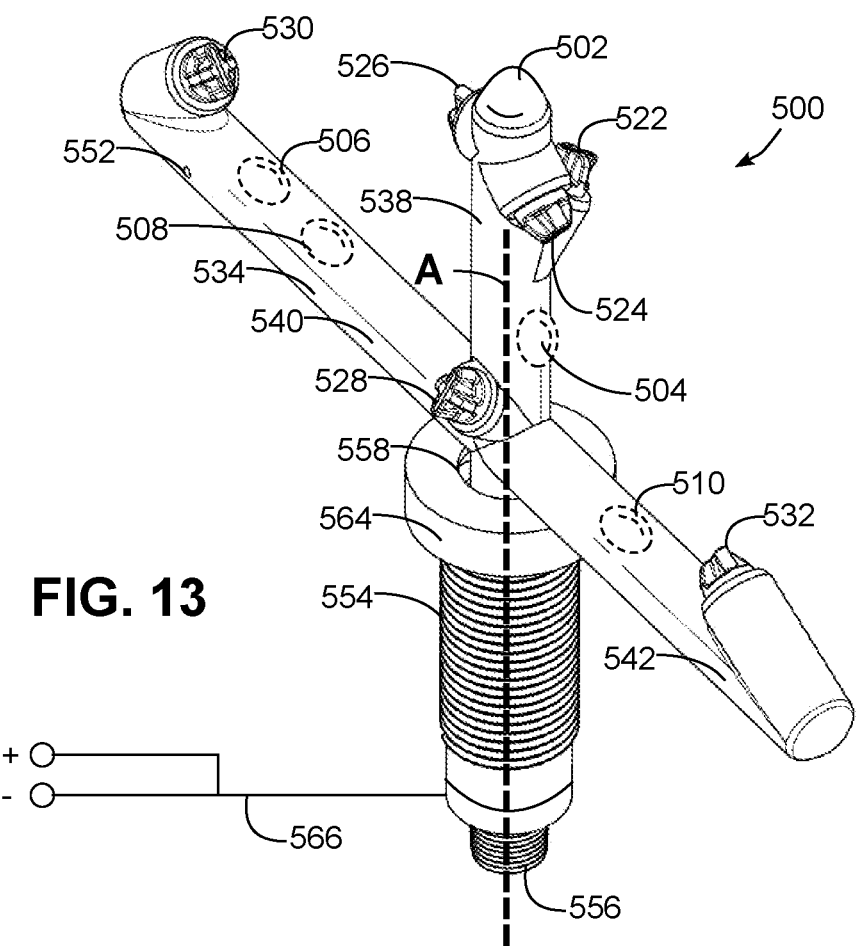
FIG. 13 is a side perspective view of an example implementation of a pop-up sprayer/ultraviolet sanitizer assembly suitable for use in the beverage container washing system of FIG. 1.

In addition, as noted above, it may be desirable in some embodiments to incorporate one or more pop-up ultraviolet sanitizers to emit ultraviolet light onto one or more interior surfaces of a beverage container. FIG. 13, for example, illustrates an example pop-up sprayer/ultraviolet sanitizer assembly 500 consistent with some embodiments of the invention, and suitable for use in lieu of sprayer 38 of beverage container washing system 10 of FIGS. 1-2. In this embodiment, the pop-up sprayer/ultraviolet sanitizer assembly includes both a sprayer including one or more nozzles and an ultraviolet sanitizer including one or more ultraviolet lights disposed thereon, and effectively operates as both a pop-up sprayer that is capable of both spraying wash fluid into the interior of a beverage container and a pop-up ultraviolet sanitizer capable of emitting ultraviolet light onto interior surfaces of the beverage container, either concurrently or sequentially. In this embodiment, pop-up sprayer/ultraviolet sanitizer assembly 500 is capable of rotating about an axis of rotation, which in the illustrated embodiment is coincident with axis of rotation A about which inner concentric housing member 62 rotates, as well as move between retracted and extended positions along the axis of rotation. Pop-up sprayer/ultraviolet sanitizer assembly 500 includes one or more ultraviolet lights and one or more nozzles, e.g., ultraviolet light 502 and six nozzles 522, 524, 526, 528, 530 and 532.

Ultraviolet light 502 is configured to emit ultraviolet light into an interior of a beverage container when the beverage container is held by the holder, thereby sanitizing an interior surface of the beverage container.

In addition, in the illustrated embodiment, and as will become more apparent below, at least one of the nozzles (e.g., nozzle 522) is an interior nozzle oriented to spray wash fluid into an interior of a beverage container when the beverage container is held by the holder, and at least one of the nozzles (e.g., nozzle 530) is a lip nozzle oriented to spray wash fluid onto an outer lip of the beverage container when the beverage container is held by the holder.

Figure 14:
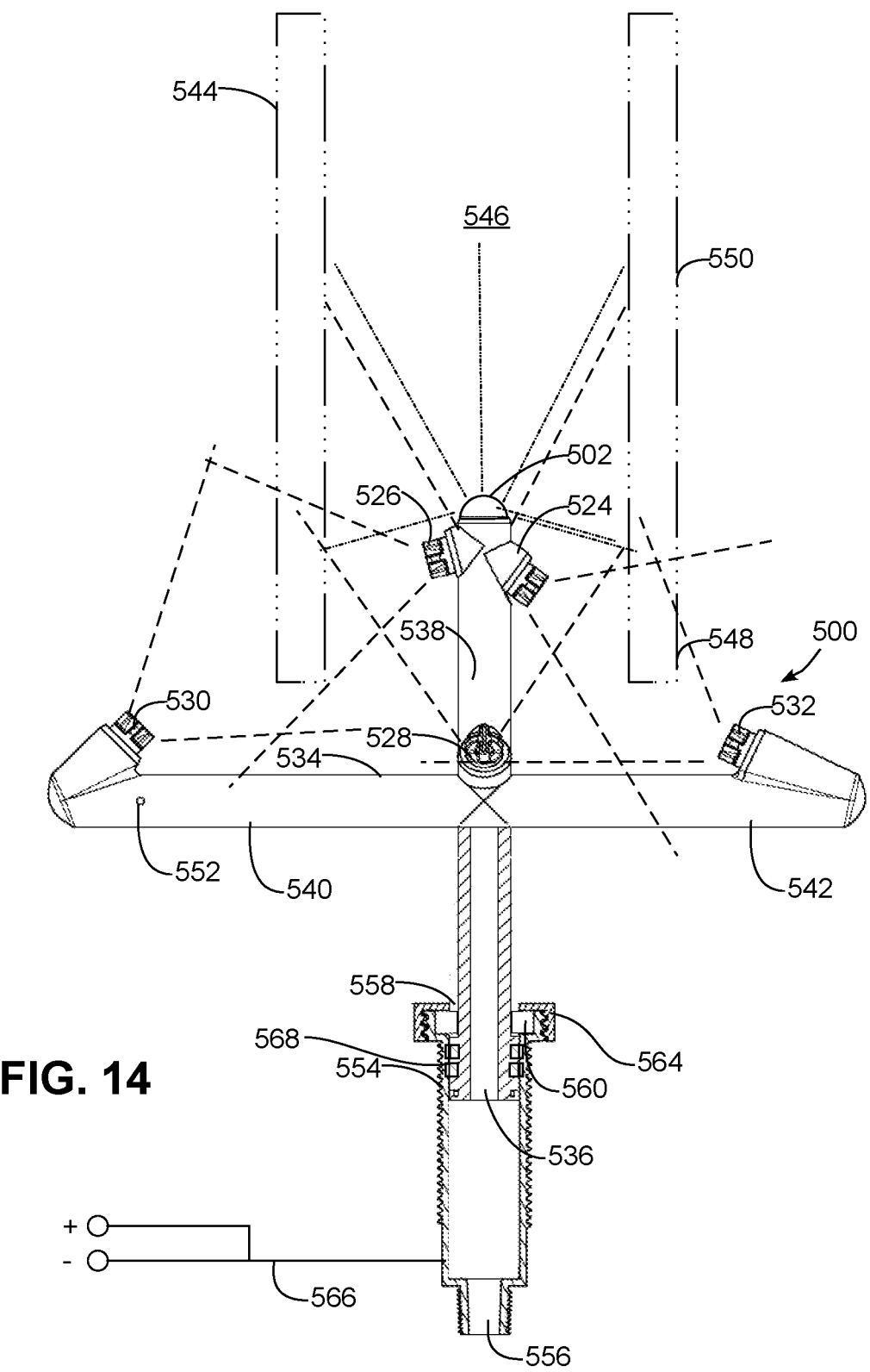
FIG. 14 is a side elevational view of the pop-up sprayer and ultraviolet sanitizer of FIG. 13, with a vertical cross section taken through the base thereof.

In the illustrated embodiment, and with additional reference to FIG. 14, ultraviolet light 502 and nozzles 522-532 of pop-up sprayer/ultraviolet sanitizer assembly 500 are supported by a manifold 534 including an inlet 536 configured to receive a pressurized wash fluid, an axial conduit 538 extending generally along the axis of rotation, and a pair of transverse conduits 540, 542 extending generally transverse to the axis of rotation, with each of conduits 538, 540, 542 in fluid communication with inlet 536.

Nozzles 522-528 are referred to herein as interior nozzles and are supported by, and in fluid communication with inlet 536 through, axial conduit 538, and at least a subset of these interior nozzles is axially offset from inlet 536 along the axis of rotation. While some of the wash fluid emitted by interior nozzles 522-528 may impact other regions of a beverage container (e.g., beverage container 544 of FIG. 14), interior nozzles 522-528 are primarily configured to spray wash fluid into the interior 546 of the beverage container, and as illustrated in FIG. 14, are generally arranged to provide overlapping spray patterns for different elevations within the interior of beverage container 544. The spray patterns may differ from one another along the axis of rotation, and the nozzles 522-528 may be axially and/or angularly offset from one another as shown in FIGS. 13 and 14.

In the illustrated embodiment, for example, interior nozzle 528 may be disposed proximate a junction between axial conduit 538 and transverse conduits 540, 542, and may have a spray pattern that is oriented to spray wash fluid onto the inner lip of the beverage container when the beverage container is held by the holder. Interior nozzles 522, 524 and 526 may also be positioned proximate the distal end of axial conduit 538, with interior nozzles 524 and 526 angularly offset from one another by about 180 degrees and having spray patterns oriented to spray wash fluid onto the inner lip of the beverage container when the beverage container is held by the holder, and interior nozzle 522 may have a spray pattern that is directed generally upwardly to spray the interior of the beverage container.

Nozzles 530, 532 are referred to herein as lip nozzles and are supported by, and in fluid communication with inlet 536 through, transverse conduits 540, 542, respectively. Each nozzle 530, 532 is radially offset from inlet 536 relative to the axis of rotation, and while some of the wash fluid emitted by lip nozzles 530, 532 may impact other regions of a beverage container, each lip nozzle 530, 532 is primarily configured to spray wash fluid at least partially onto an outer lip 548 of the beverage container 544, i.e., a portion of the beverage container lip or opening formed by an outer surface 550 of beverage container 544. As seen in FIG. 14, each lip nozzle 530, 532 may also focus spray onto other portions of the beverage container lip (e.g., an interior lip portion formed by an inner surface of the beverage container), and it will be appreciated that since it is generally the areas around the lip where a user's mouth may come into contact with the beverage container, lip nozzles 530, 532 in some embodiments may focus their efforts on spraying wash fluid at a sanitizing temperature to appropriately sanitize the areas of the beverage container that a user may likely come into contact with when drinking from the beverage container.

In the illustrated embodiment, transverse conduits 540, 542 are angularly offset from one another by about 180 degrees and both extend substantially normal to the axis of rotation. In other embodiments, different numbers of transverse conduits, e.g., as few as one or more than two, may be used, and the transverse conduits may extend at differing angles relative to the axis of rotation, so the invention is not limited to the particular configuration illustrated herein.

Ultraviolet light 502 may be proximate a distal end of axial conduit 538 from inlet 536 and have a beam width with a center that is oriented along the axis of rotation. In addition, with reference to FIG. 13, in some embodiments, multiple ultraviolet lights may be used, and ultraviolet lights may be disposed on other portions of the assembly in lieu of or in addition to the position of ultraviolet light 502, e.g., as illustrated by ultraviolet light 504 (which is disposed on a side of axial conduit 538) and ultraviolet lights 506, 508 and 510, which are disposed on sides of transverse conduits 540, 542. It will be appreciated that each ultraviolet light 502-510 may each include one or more UV LEDs arranged to emit ultraviolet light with an intensity and a distribution that is sufficient to sanitize the interior surfaces of a beverage container. Power to ultraviolet light 502 may be provided, for example, through leads 566 that supply power to ultraviolet light 502 through a slip ring arrangement 568. Additional leads (not shown separately in FIGS. 13-14) may run within or along the walls of a base 554 and manifold 534 to convey power from leads 566 to slip ring arrangement 568 and onto ultraviolet light 502.

In addition, in the illustrated embodiment, pop-up sprayer/ultraviolet sanitizer assembly 500 may additionally include one or more drive nozzles 552 that emit wash fluid in a tangential direction relative to the axis of rotation to drive rotation of pop-up sprayer/ultraviolet sanitizer assembly 500 when spraying wash fluid. In other embodiments, the wash fluid sprayed by another nozzle 522-532 may impart sufficient torque to rotate the sprayer, and separate drive nozzles 552 may not be used. Further, in some embodiments an electric motor, pressurized air, or other electromechanical or mechanical drive system may be used to rotate the assembly and/or move the assembly between retracted and extended positions, whereby no separate drive nozzles 552 may be used.

Also in the illustrated embodiment, each nozzle 522-532 is a screw-in nozzle and is configured to threadably engage corresponding threaded apertures in manifold 534, and ultraviolet light 502 includes a threaded mount capable of engaging with a corresponding threaded aperture in manifold 534. As such, it may be desirable to form manifold 534 from a material capable of threadably engaging ultraviolet light 502 and nozzles 522-532, e.g., metal. Each nozzle 522-532 also is configured with a fan spray pattern, e.g., with a spray width of about 15 to about 50 degrees in some embodiments. All nozzles 522-532 may be similarly configured in some embodiments, while in other embodiments, each nozzle 522-532 may include a different nozzle configuration tailored for its particular location and direction of spray. In the illustrated embodiment, the nozzles 522-532 are also clocked to a particular angle, e.g., such that the fan jets overlap and are all primarily oriented in the Y-plane. It will be appreciated that pop-up sprayer/ultraviolet sanitizer assembly 500 may utilize different numbers, locations, types and configurations of nozzles in other embodiments, so the invention is not limited to the specific arrangement of nozzles illustrated herein. For example, in some embodiments, nozzles may be integrally molded into a manifold, and in some embodiments, different spray patterns, e.g., fluidic nozzles, jet nozzles, etc., may be used.

It will also be appreciated that, in the illustrated embodiment, pop-up sprayer/ultraviolet sanitizer assembly 500 is predominantly limited to spraying wash fluid onto the interior of a beverage container as well as the inner and outer lip thereof (e.g., about 1 inch of the outer surface of the beverage container proximate the lip). While other regions of the outside of the beverage container may come into contact with wash fluid in some instances, the focus of assembly pop-up sprayer/ultraviolet sanitizer 500 is on the areas of the beverage container that either come into contact with a beverage consumed by a user or come into contact with a user's mouth. In other embodiments, however, additional sprayers, e.g., located around the perimeter of the wash chamber, may be used to focus wash fluid onto the outside of a beverage container.

Manifold 534 is slidably received in a base 554. Base 554 includes an inlet 556 that receives pressurized wash fluid from pump 138, and an opening 558 that slidably and rotatably receives manifold 534. A seal 560 is disposed on base 554 to seal opening 558, while still allowing for slidable and rotary movement of manifold 534. A bias mechanism (not shown), e.g., a spring, may be used to bias manifold 534, and thus pop-up sprayer/ultraviolet sanitizer assembly 500, to a retracted position, e.g., as illustrated in FIG. 13. Manifold 534 is configured to overcome any bias mechanism and slide within base 554 to an extended position, e.g., as illustrated in FIG. 14, as a result of the pressure generated by wash fluid received through inlet 556 of base 554.

Seal 560 in some embodiments may be a seal collar with living hinge, and a screw cap 564 may be used in some embodiments to secure manifold 534 within base 554. It will be appreciated that, given the high pressure utilized in some embodiments, other sealing arrangements may be used to minimize fluid and pressure loss through opening 558. In addition, while a bias mechanism may be configured as a spring in some embodiments, other manners of biasing the sprayer to the retracted position may be used in other embodiments, e.g., a gravity bias mechanism that allows the manifold to drop to the retracted position based upon the weight of the manifold 534 and nozzles 520-532. Further, as noted above, in some embodiments an electric motor, solenoid, pressurized air, or other electromechanical or mechanical drive system may be used in some embodiments to transition pop-up sprayer/ultraviolet sanitizer assembly 500 between the extended and retracted positions. Therefore, the invention is not limited to the particular design illustrated herein.

Therefore, it may be seen that pop-up sprayer/ultraviolet sanitizer assembly 500 effectively provides a pop-up ultraviolet sanitizer integrated into the same assembly with one or more nozzles of a sprayer to allow for the ultraviolet sanitizer to be moved between retracted and extended positions along an axis of extension thereof (which in the embodiment of FIGS. 13-14 is coaxial with the axis of rotation of the sprayer), and such that when in the extended position at least a portion of the ultraviolet sanitizer extends into an opening of a beverage container to enable one or more ultraviolet lights thereof to emit ultraviolet light onto an interior surface of the beverage container.

It will be appreciated, however, that while a pop-up ultraviolet sanitizer consistent with the invention is generally used with one or more sprayers in order to wash and sanitize a beverage container, a pop-up ultraviolet sanitizer need not be integrated with a sprayer in other embodiments.

Figure 15:
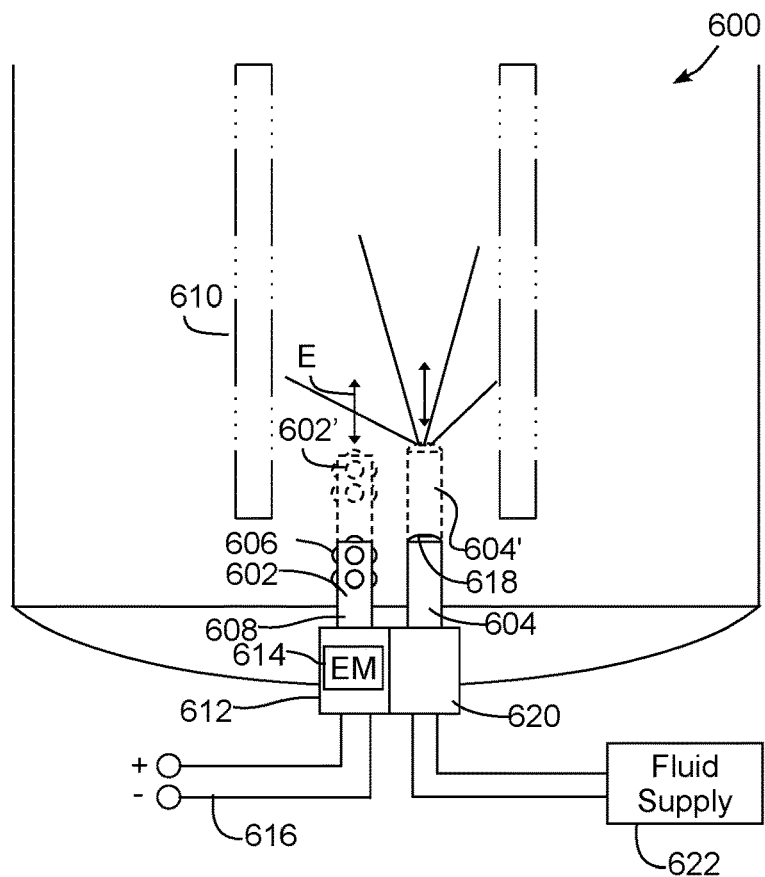
FIG. 15 is a functional side elevational view of another example implementation of a beverage container washing system consistent with the invention, and including a pop-up ultraviolet sanitizer adjacent to a pop-up sprayer.

For example, as illustrated by beverage container washing system 600 of FIG. 15, in some embodiments it may be desirable to implement a pop-up ultraviolet sanitizer 602 separate from and adjacent to a pop-up sprayer 604. Pop-up ultraviolet sanitizer 602, for example, may be extendible from a retracted position to an extended position represented at 602' and may include one or more ultraviolet lights 606 disposed on a wand 608 and having a sufficient coverage to appropriately sanitize the interior surfaces of a beverage container 610. Wand 608 is supported on a base 612 and an extension mechanism 614 is used to extend and retract the wand 608 along an extension axis E. The extension mechanism 614 may be, for example, an electric motor (e.g., a stepper motor, a DC motor and switch, a DC motor and reed position switch, etc.), a solenoid, a magnetic drive, a pneumatic drive, a hydraulic drive, or practically any other suitable mechanism for translating the wand 608 along extension axis E. In some embodiments, for example, air pressure generated for an air knife may be used to provide pneumatic pressure for extending wand 608. In addition, a bias mechanism may be used in some embodiments to bias the wand 608 to either the retracted or extended position. Power to ultraviolet lights 606 may also be supplied through leads 616.

Pop-up sprayer 604 may include one or more nozzles 618 and may be supported by a base 620 and provided with fluid from a fluid supply 622. In addition, fluid pressure may be used to extend pop-up sprayer 604 to an extended position as illustrated at 604', e.g., in a similar manner to pop-up sprayer/ultraviolet sanitizer assembly 500 of FIGS. 13-14. In other embodiments, however, other manners of extending pop-up sprayer 604 may be used, e.g., an electric motor, solenoid, magnetic drive, pneumatic drive, etc. In addition, in some embodiments, the sprayer for the interior of beverage container 610 may not be extendible, and instead be stationary or may rotate about an axis without extending into the beverage container.

It will be appreciated that in order to enable each of pop-up ultraviolet sanitizer 602 and pop-up sprayer 604 to extend into a beverage container having a relatively narrow opening, each of the components may desirably be relatively narrow and relatively in close proximity to one another so as to both be able to extend into the opening.

Figure 16:
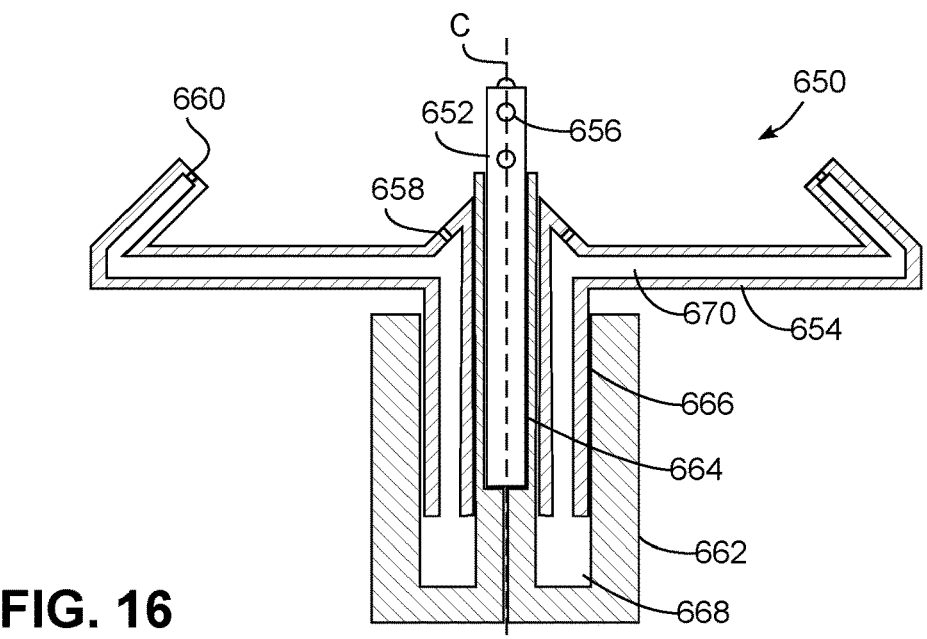
FIG. 16 is a functional side cross-sectional view of another example implementation of a pop-up sprayer/ultraviolet sanitizer assembly consistent with the invention, and including a pop-up ultraviolet sanitizer coaxial with a pop-up sprayer and being independently extended therefrom.
Figure 17:
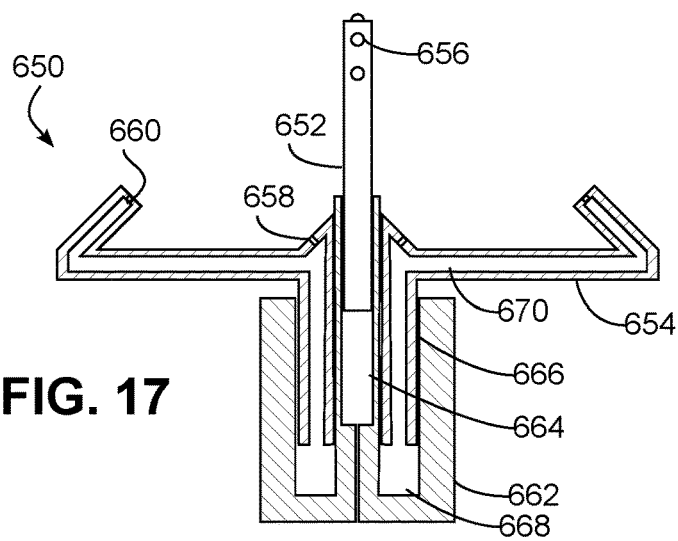
FIG. 17 is a functional side cross-sectional view of the pop-up sprayer/ultraviolet sanitizer assembly of FIG. 16, with the pop-up ultraviolet sanitizer thereof extended.
Figure 18:
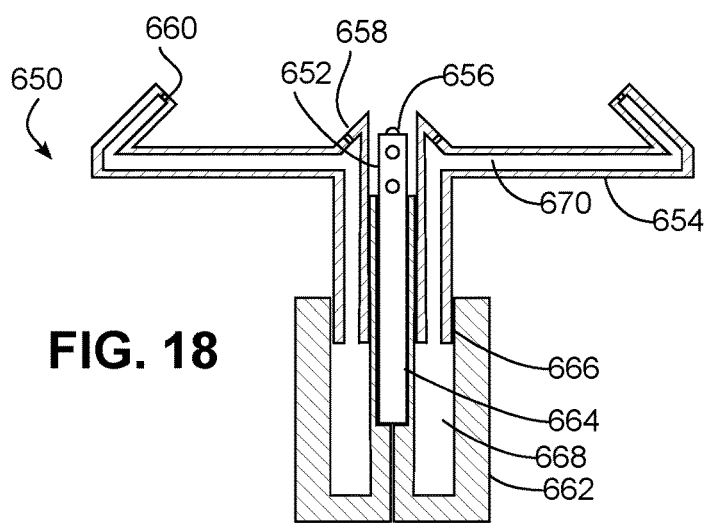
FIG. 18 is a functional side cross-sectional view of the pop-up sprayer/ultraviolet sanitizer assembly of FIG. 16, with the pop-up sprayer thereof extended.

In other embodiments, rather than positioning a pop-up ultraviolet sanitizer adjacent to a sprayer such as a pop-up sprayer, a pop-up ultraviolet sanitizer may be coaxial with a sprayer, e.g., as shown in FIGS. 16-18. FIG. 16, in particular, illustrates a pop-up sprayer/ultraviolet sanitizer assembly 650 including a pop-up ultraviolet sanitizer 652 that is coaxial with a pop-up sprayer 654, with both extending generally along an axis C. Pop-up ultraviolet sanitizer 652 may include one or more ultraviolet lights 656, each including one or more ultraviolet emitters (e.g., UV LEDs), and pop-up sprayer 654 may include one or more nozzles, e.g., nozzles 658, 660. Both pop-up ultraviolet sanitizer 652 and pop-up sprayer 654 are supported by a base 662, with pop-up ultraviolet sanitizer 652 supported in an inner sleeve 664 and pop-up sprayer 654 supported in an outer, annular sleeve 666. A fluid inlet 668 in base 662 may supply fluid to a manifold 670 in pop-up sprayer 654 to convey fluid to each nozzle 658, 660, and in some embodiments, to provide sufficient fluid pressure to extend pop-up sprayer 654 (as shown in FIG. 18). In other embodiments, other manners of extending pop-up sprayer as discussed above, e.g., a motor, magnetic drive, solenoid, or air pressure, may be used.

Extension of pop-up sanitizer 652 (e.g., as shown in FIG. 17) may be implemented in a number of manners, e.g., using various types of extension mechanisms such as an air or liquid fluid supply 672, solenoid 674 or motor 676 (FIG. 16), or in other suitable manners described herein. Thus, it will be appreciated that each of pop-up sanitizer 652 and pop-up sprayer 654 may be independently actuated in the embodiment of FIGS. 16-17, allowing for sequential, or in some instances, concurrent washing and ultraviolet irradiation.

Figure 19:
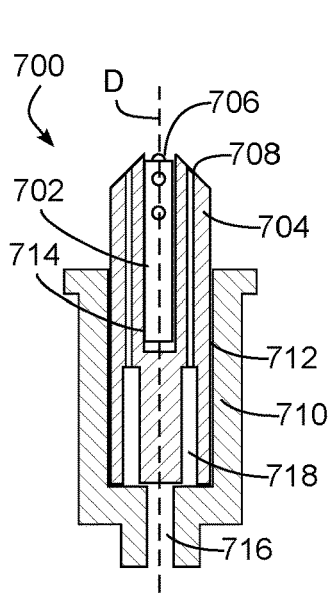
FIG. 19 is a functional side cross-sectional view of another example implementation of a pop-up sprayer/ultraviolet sanitizer assembly consistent with the invention, and including a pop-up ultraviolet sanitizer coaxial with a pop-up sprayer and being partially extendible therewith.

In still other embodiments, it may also be desirable for a pop-up ultraviolet sanitizer to be supported by a pop-up sprayer, such that at least a portion of the extendible range of the pop-up ultraviolet sanitizer is based upon extension of a pop-up sprayer upon which the pop-up ultraviolet sanitizer is supported. FIG. 19, for example, illustrates a pop-up sprayer/ultraviolet sanitizer assembly 700 including a pop-up ultraviolet sanitizer 702 that is coaxial with and supported by a pop-up sprayer 704, with both extending generally along an axis D. Pop-up ultraviolet sanitizer 702 may include one or more ultraviolet lights 706, each including one or more ultraviolet emitters (e.g., UV LEDs), and pop-up sprayer 704 may include one or more nozzles, e.g., nozzles 708. Pop-up sprayer 704 is supported by a base 710, e.g., within a sleeve 712 in base 710, while pop-up ultraviolet sanitizer 702 is supported by pop-up sprayer 704, e.g., within a sleeve 714 in pop-up sprayer 704. A fluid inlet 716 in base 710 may supply fluid to a manifold 718 in pop-up sprayer 704 to convey fluid to each nozzle 708, and in some embodiments, to provide sufficient fluid pressure to extend pop-up sprayer 704. In other embodiments, other manners of extending pop-up sprayer as discussed above, e.g., a motor, magnetic drive, solenoid, or air pressure, may be used.

Figure 20:
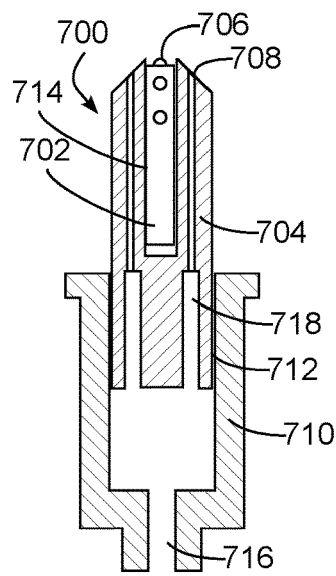
FIG. 20 is a functional side cross-sectional view of the pop-up sprayer/ultraviolet sanitizer assembly of FIG. 19, with the pop-up sprayer thereof extended.
Figure 21:
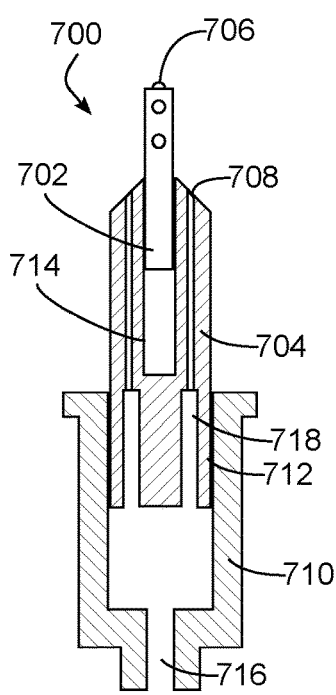
FIG. 21 is a functional side cross-sectional view of the pop-up sprayer/ultraviolet sanitizer assembly of FIG. 19, with each of the pop-up sprayer and the pop-up ultraviolet sanitizer thereof extended.

Extension of pop-up sanitizer 702 may be implemented in a number of manners, e.g., using any of the aforementioned extension mechanisms described above in connection with FIG. 16. In addition, it will be appreciated that extension of pop-up sprayer 704, as shown in FIG. 20, may similarly extend pop-up ultraviolet sanitizer 702 along axis D. Thereafter, extension of pop-up ultraviolet sanitizer 702 may further extend the pop-up ultraviolet sanitizer 702 along axis D, as shown in FIG. 21. As such, a portion of the extension range of pop-up ultraviolet sanitizer 702 is implemented through extension of pop-up sprayer 702. It will also be appreciated that, while pop-up sanitizer 702 and pop-up sprayer 704 may be independently actuated and/or extended in some embodiments, in other embodiments, the actuation and/or extension of both components may be cooperatively performed, e.g., where the pressure of the fluid supplied to pop-up sprayer 704 is sufficient to extend both pop-up sprayer 704 and pop-up ultraviolet sanitizer 702 as well as supply sufficient fluid for nozzles 708.

It may also be seen from FIGS. 19-21 that in some embodiments, a pop-up sprayer and/or pop-up ultraviolet sanitizer need not be rotatable. Furthermore, it may be seen that in some embodiments, a pop-up ultraviolet sanitizer may be fully retracted into a sleeve of a base or pop-up sprayer in some embodiments, or may partially extend out of the sleeve in some embodiments, exposing one or more ultraviolet lights, and thus being usable even when in a retracted position. Some embodiments may also support multiple, partially-extended positions for a pop-up ultraviolet sanitizer. In addition, while the coaxial embodiments illustrated herein incorporate a pop-up ultraviolet sanitizer that is circumscribed by a pop-up sprayer, in other embodiments a pop-up sprayer may be circumscribed, and contained within a pop-up ultraviolet sanitizer.

Other modifications may be made to the illustrated embodiments without departing from the spirit and scope of the invention. Therefore, the invention lies in the claims hereinafter appended.

What is claimed is:

1. An apparatus for washing a beverage container, comprising:
   a housing defining a wash chamber;
   a holder disposed within the wash chamber and configured to hold the beverage container during a washing operation;
   a sprayer disposed in the wash chamber and including at least one nozzle, the at least one nozzle oriented to spray wash fluid onto the beverage container when the beverage container is held by the holder; and
   a pop-up ultraviolet sanitizer disposed in the wash chamber and including at least one ultraviolet light, the pop-up ultraviolet sanitizer configured to move between retracted and extended positions along an axis of extension thereof, wherein when in the extended position at least a portion of the pop-up ultraviolet sanitizer extends into an opening of the beverage container when the beverage container is held by the holder to emit ultraviolet light onto an interior surface of the beverage container;
   wherein the sprayer includes a pop-up sprayer configured to rotate about an axis of rotation and to move between retracted and extended positions along the axis of rotation;
   wherein the pop-up ultraviolet sanitizer and the pop-up sprayer are disposed on a pop-up sprayer/ultraviolet sanitizer assembly, and wherein the axis of extension of the pop-up ultraviolet sanitizer and the axis of rotation of the pop-up sprayer are substantially coaxial with one another; and
   wherein the pop-up ultraviolet sanitizer is movable relative to the pop-up sprayer along the axis of extension.

2. An apparatus for washing a beverage container, comprising:
   a housing defining a wash chamber;
   a holder disposed within the wash chamber and configured to hold the beverage container during a washing operation;
   a sprayer disposed in the wash chamber and including at least one nozzle, the at least one nozzle oriented to spray wash fluid onto the beverage container when the beverage container is held by the holder; and
   a pop-up ultraviolet sanitizer disposed in the wash chamber and including at least one ultraviolet light, the pop-up ultraviolet sanitizer configured to move between retracted and extended positions along an axis of extension thereof, wherein when in the extended position at least a portion of the pop-up ultraviolet sanitizer extends into an opening of the beverage container when the beverage container is held by the holder to emit ultraviolet light onto an interior surface of the beverage container;
   wherein the sprayer includes a pop-up sprayer configured to rotate about an axis of rotation and to move between retracted and extended positions along the axis of rotation; and
   wherein the at least one nozzle includes an interior nozzle disposed on the pop-up sprayer and oriented to spray wash fluid into an interior of the beverage container when the beverage container is held by the holder and a lip nozzle disposed on the pop-up sprayer and oriented to spray wash fluid onto an outer lip of the beverage container when the beverage container is held by the holder.

3. The apparatus of claim 2, wherein the pop-up sprayer includes a manifold including an inlet configured to receive a wash fluid, an axial conduit extending generally along the axis of rotation, and a transverse conduit extending generally transverse to the axis of rotation, wherein the axial and transverse conduits are in fluid communication with the inlet, wherein the interior nozzle is in fluid communication with the inlet through the axial conduit and is axially offset from the inlet along the axis of rotation, and wherein the lip nozzle is in fluid communication with the inlet through the transverse conduit and radially offset from the inlet relative to the axis of rotation.

4. The apparatus of claim 3, wherein the lip nozzle is a first lip nozzle and the transverse conduit is a first transverse conduit, wherein the manifold further includes a second transverse conduit extending generally transverse to the axis of rotation and angularly offset from the first transverse conduit, wherein at least one nozzle further includes a second lip nozzle oriented to spray wash fluid onto the outer lip of the beverage container when the beverage container is held by the holder, the second lip nozzle in fluid communication with the inlet through the second transverse conduit and radially offset from the inlet relative to the axis of rotation, wherein the first and second transverse conduits are angularly offset from one another by about 180 degrees and extend substantially normal to the axis of rotation.

5. The apparatus of claim 4, wherein at least one of the first and second transverse conduits includes at least one drive nozzle configured to emit wash fluid in a tangential direction relative to the axis of rotation to drive rotation of the pop-up sprayer about the axis of rotation when spraying wash fluid from the pop-up sprayer.

6. The apparatus of claim 3, wherein the pop-up ultraviolet sanitizer and the pop-up sprayer are disposed on a pop-up sprayer/ultraviolet sanitizer assembly.

7. The apparatus of claim 6, wherein the at least one ultraviolet light of the pop-up ultraviolet sanitizer is disposed on an end or side of the axial conduit.

8. The apparatus of claim 6, wherein the at least one ultraviolet light of the pop-up ultraviolet sanitizer is disposed on the transverse conduit.

9. The apparatus of claim 1, wherein the pop-up sprayer/ultraviolet sanitizer assembly includes a base, wherein the pop-up sprayer is supported by the base.

10. The apparatus of claim 9, wherein the pop-up sprayer is supported in a first sleeve in the base, and wherein the pop-up ultraviolet sanitizer is supported in a second sleeve in the base.

11. The apparatus of claim 10, wherein the pop-up ultraviolet sanitizer and the pop-up sprayer are independently extendible from the base.

12. The apparatus of claim 9, wherein the pop-up ultraviolet sanitizer is supported by the pop-up sprayer in a sleeve in the pop-up sprayer, wherein a portion of an extension range of the pop-up ultraviolet sanitizer is provided by extension of the pop-up sprayer along the axis of rotation.

13. The apparatus of claim 2, wherein the pop-up ultraviolet sanitizer is separate from and adjacent to the sprayer.

14. The apparatus of claim 13, wherein the axis of extension is parallel to and separated from the axis of rotation.

15. The apparatus of claim 1, wherein the pop-up ultraviolet sanitizer is configured to rotate about the axis of extension and is supported by a base, the pop-up ultraviolet sanitizer further comprising a slip ring arrangement electrically coupling the pop-up ultraviolet sanitizer to the base to provide power to the at least one ultraviolet light.

16. The apparatus of claim 1, wherein the pop-up ultraviolet sanitizer includes an extension mechanism configured to selectively extend the pop-up ultraviolet sanitizer.

17. The apparatus of claim 16, wherein the extension mechanism includes a stepper motor, a DC motor, a solenoid, a magnetic drive, a pneumatic drive, or a hydraulic drive.

18. A pop-up sprayer/ultraviolet sanitizer assembly for washing a beverage container disposed in a wash chamber, the assembly comprising:
a sprayer configured to rotate about an axis of rotation, the sprayer disposed in the wash chamber and including at least one nozzle, the at least one nozzle oriented to spray wash fluid onto the beverage container when the beverage container is positioned in the wash chamber; and
at least one ultraviolet light;
wherein each of the sprayer and the at least one ultraviolet light is configured to selectively extend along the axis of rotation of the sprayer, wherein when the sprayer is extended, the at least one nozzle is positioned to extend through an opening of the beverage container and spray wash fluid into an interior of the beverage container, and when the at least one ultraviolet light is extended, the at least one ultraviolet light is positioned to emit ultraviolet light onto an interior surface of the beverage container and
wherein the ultraviolet light is movable relative to the sprayer along the axis of rotation.

* * * * *